US009073920B2

(12) United States Patent
Cushman et al.

(10) Patent No.: US 9,073,920 B2
(45) Date of Patent: Jul. 7, 2015

(54) SUBSTITUTED DIBENZONAPHTHYRIDINES, PHARMACEUTICAL USES THEREOF AND PROCESSES THERFOR

(75) Inventors: Mark S. Cushman, West Lafayette, IN (US); Evgeny A. Kiselev, West Lafayette, IN (US)

(73) Assignee: Purdue Research Foundation, Lafayette, IN (US)

( * ) Notice: Subject to any disclaimer, the term of this patent is extended or adjusted under 35 U.S.C. 154(b) by 0 days.

(21) Appl. No.: 13/816,972

(22) PCT Filed: Aug. 17, 2011

(86) PCT No.: PCT/US2011/048138
§ 371 (c)(1),
(2), (4) Date: Feb. 14, 2013

(87) PCT Pub. No.: WO2012/024437
PCT Pub. Date: Feb. 23, 2012

(65) Prior Publication Data
US 2013/0143878 A1 Jun. 6, 2013

Related U.S. Application Data

(60) Provisional application No. 61/374,430, filed on Aug. 17, 2010.

(51) Int. Cl.
*C07D 471/04* (2006.01)

(52) U.S. Cl.
CPC .................................. *C07D 471/04* (2013.01)

(58) Field of Classification Search
CPC ..................................................... C07D 471/04
USPC ............................................ 546/70; 514/285
See application file for complete search history.

(56) References Cited

U.S. PATENT DOCUMENTS

| 5,239,075 | A | 8/1993 | Audia et al. |
| 5,597,831 | A | 1/1997 | Michalsky et al. |
| 6,509,344 | B1 | 1/2003 | Cushman et al. |
| 7,312,228 | B2 | 12/2007 | Cushman et al. |
| 7,495,100 | B2 | 2/2009 | Cushman et al. |
| 7,781,445 | B2 | 8/2010 | Cushman et al. |
| 8,053,443 | B2 | 11/2011 | Cushman et al. |
| 2004/0229895 | A1 | 11/2004 | Jagtap et al. |
| 2008/0214576 | A1 | 9/2008 | Matteucci et al. |
| 2008/0262016 | A1 | 10/2008 | Jagtap et al. |
| 2008/0318995 | A1 | 12/2008 | Cushman et al. |
| 2009/0258890 | A1 | 10/2009 | Lavoie et al. |
| 2012/0302563 | A1 | 11/2012 | Cushman et al. |

FOREIGN PATENT DOCUMENTS

| WO | WO 2004/014862 | 2/2004 |
| WO | WO 2004/014906 | 2/2004 |
| WO | WO 2004/014918 | 2/2004 |
| WO | WO 2012/162513 | 11/2012 |

OTHER PUBLICATIONS

Stadlbauer et al. (CAPLUS Abstract of: Monatshefte fuer Chemie (1984), 115(4), 467-75).*
Kubinyi (3D QSAR in Drug Design: Ligand-Protein Interactions and Molecular Similarity, vol. 2-3, Springer, 1998, 800 pages). p. 243-44 provided.*
Wermuth, The Practice of Medicinal Chemsitry, 2d ed. (2003), 768 pages. Chs. 9-10 provided.*
Staker, B.L.; Hjerrild, K.; Feese, M.D.; Behnke, C.A.; Burgin Jr., A.B.; Stewart, L. "The Mechanism of Topoisomerase I Poisoning by a Camptothecin Analog," *Proc. Natl. Acad. Sci. U.S.A.*, 2002, 99, 15387-15392.
Pommier, Y.; Pourquier, P.; Fan, Y.; Strumberg, D. "Mechanism of Action of Eukaryotic DNA Topoisomerase I and Drugs Targeted to the Enzyme," *Biochim. Biophys. Acta*, 1998, 1400, 83-106.
Kohlhagen, G.; Paull, K.; Cushman, M.; Nagafuji, P.; Pommier, Y., "Protein-Linked DNA Strand Breaks Induced by NSC 314622, a Novel Noncamptothecin Topoisomerase I Poison," *Mol. Pharmacol.*, 1998, 54, 50-58.
Jaxel, C.; Kohn, K. W.; Wani, M. C.; Wa.., M.C.; Pommier, Y., "Structure-Activity Study of the Actions of Camptothecin Derivatives on Mammalian Topoisomerase I: Evidence for a Specific Receptor Site and a Relation to Antitumor Activity," *Cancer. Rev.*, 1989, 49, 1465-1469.
Minami, H.; Beijnen, J.H.; Verweij, J.; Ratain, M. J., "Limited Sampling Model for the Area under the Concentration Time Curve of Total Topotecan," *Clin. Cancer Res.*, 1996, 2, 43-46.
Danks, M.K.; Pawlik, C.A.; Whipple, D.O.; Wolverton, J.S., "Intermittant Exposure of Medulloblastoma Cells to Topotecan Produces Growth Inhibition equivalent to Continuous Exposure," Clinical Cancer Research, 1997, 3, 1731-1738.
Haas, N.B.; LaCreta, F.P.; Walczak, J.; Hudes, G.R.; Brennan, J.M.; Ozols, R.F.; O'Dwyer, P.J. "Phase 1/Pharmacokinetic Study of Topotecan by 24-Hour Continuous Infusion Weekly," *Cancer Res.*, 1994, 54, 1220-1226.
Shapiro, S.L.; Geiger, K.; Youlus, J.; Freedman, L., "Indandiones. II. A Modified Dieckmann Reaction," *J. Org. Chem.*, 1961, 26, 3580-3582.
Pailer, M.; Worther, H.; Meller, A., "Some reactions of 2-aryl-1,3-indandiones," *Monatsh Chem.*, 1961, 92, 1037-1047.
Freireich, E.J., et al., "Quantitative Comparison to Toxicity of Anticancer Agents in Mouse, Rat, Hamster, Dog, Monkey, and Man," *Cancer Chemother. Rep.*, 1966, 50 (4), 219-244.

(Continued)

*Primary Examiner* — Robert Havlin
(74) *Attorney, Agent, or Firm* — Mark S. Cohen; Pearl Cohen Zedek Latzer Baratz LLP

(57) ABSTRACT

The invention described herein pertains to substituted dibenzonaphthyridine compounds, pharmaceutical compositions, and formulations comprising the dibenzonaphthyridine compounds, their synthesis, and methods for their use in the treatment and/or prevention of cancer.

16 Claims, No Drawings

(56) References Cited

OTHER PUBLICATIONS

Nagarajan, M.; Xiao, X.; Antony, S.; Kohlhagen, G.; Pommier, Y.; Cushman, M., "Design, Synthesis, and Biological Evaluation of Indenoisoquinoline Topoisomerase I Inhibitors Featuring Polyamine Side Chains on the Lactam Nitrogen," *J. Med. Chem,.* 2003, 46, 5712-5724.

Hollingshead, M.; Plowman, J.; Alley, M.; Mayo, J.; Sausville, E., "The Hollow Fiber Assay," *Contrib. Oncol,.* 1999, 54, 109-120.

Plowman, J.; Camalier, R.; Alley, M.; Sausville, E.; Schepartz, S., "US NCI Testing Procedures," *Contrib. Onco,l.* 1999, 54, 121-135.

Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.*, 2003, 63, 7428-7435.

West, Anthony R., "Solid State Chemistry and its Applications," Wiley, New York, 1988, pp. 358 & 365.

Kucerova, T., et al., "Solovolysis of O-acyl-10-hydroxy-10-dihydro-indeno[1,2-c]Isoquinolin-5,11-diones," 1979, Database CA, Chemical Abstracts Service, Database Accession No. 1980:22814.

Cushman, Mark, et al., "Synthesis of a New Indeno[1,2-c]Isoquinolines: Cytotoxic Non-Camptothecin Topoisomerase I Inhibitors," 2000, *Journal of Medicinal Chemistry*, vol. 43, No. 20, pp. 3688-3698.

Jayaraman, Muthusamy, et al., "Synthesis of New Dihydroindeno[1-2-c]Isoquinolone and Indenoisoquinolinium Chloride Topoisomerase I Inhibitors Having High In Vivo Anticancer Activity in The Hollow Fiber Animal Model," 2002, *Journal of Medicinal Chemistry*, vol. 45, No. 1, pp. 242-249.

Morrell, Andrew, et al., "Synthesis, of Nitrated Indenoisoquinolines as Topoisomerase I Inhibitors," 2004, *Bioorganic & Medicinal Chemistry Letters*, vol. 14, pp. 3659-3663.

Nagarajan, Muthukaman, et al., "Synthesis and Anticancer Activity of Simplified Indenoisoquinoline Topoisomerase I Inhibitors Lacking Substituents on The Aromatic Ring," 2004, *Journal of Medicinal Chemistry*, vol. 47, No. 23, pp. 5651-5661.

Strumberg, Dirk, et al., "Synthesis of Cytotoxic Indenoisoquinoline Topoisomerase I Poisons," 1999, *Journal of Medicinal Chemistry*, vol. 42, No. 3, pp. 446-457.

Wawzonek, Stanley, "Novel Formation of 11-Ketoindeno[1,2-c]Isocoumarin," 1968, The Journal of Organic Chemistry, vol. 33, No. 2, pp. 896-897.

Wawzonek, Stanley, "Synthesis of 6-Substituted-6H-Indeno[1,2-c]Isoquinoline-5,11-diones," 1982, Database CA, Chemical Abstracts Service, Database Accession No. 1982:199485.

Cushman, Mark, and Prem Mohan. "Synthesis and antitumor activity of structural analogs of the anticancer benzophenanthridine alkaloid fagaronine chloride." *Journal of medicinal chemistry* 28.8 (1985): 1031-1036.

Wawzonek, S., J. K. Stowell, and R. E. Karll. "The Synthesis and Reactions of 1-Carbamyl-11-ketoindeno [1, 2-c] isoquirioline1." *The Journal of Organic Chemistry* 31.4 (1966): 1004-1006.

Cushman, Mark, Prem Mohan, and Edward CR Smith. "Synthesis and biological activity of structural analogs of the anticancer benzophenanthridine alkaloid nitidine chloride." *Journal of medicinal chemistry* 27.4 (1984): 544-547.

Staker et al., "Structures of Three Classes of Anticancer Agents Bound to the Human Topoisomerase I-DNA Covalent Complex," *J. Med. Chem.*, 2005, vol. 48, No. 7, 2336-2345.

Ioanoviciu et al., "Synthesis and Mechanism of Action Studies of a Series of Norindenoisoquinoline Topoisomerase I Poisons Reveal an Inhibitor with a Flipped Orientation in the Ternary DNA-Enzyme-Inhibitor Complex as Determined by X-ray Crystallographic Analysis," *J. Med. Chem.*, 2005, vol. 48, No. 15, 4803-4814.

Xiao et al., "On the Binding of Indeno[1,2-c]isoquinolines in the DNA-Topoisomerase I Cleavage Complex," *J. Med. Chem.*, 2005, vol. 48, No. 9, 3231-3238.

Antony et al., "Cellular Topoisomerase I Inhibition and Antiproliferative Activity by MJ-III-65 (NSC 706744), an Indenoisoquinoline Topoisomerase I Poison," *Molecular Pharmacology*, 2005, vol. 67, No. 2, 523-530.

Peterson, Katherine E., et al. "Alcohol-, Diol-, and Carbohydrate-Substituted Indenoisoquinolines as Topoisomerase I Inhibitors: Investigating the Relationships Involving Stereochemistry, Hydrogen Bonding, and Biological Activity," *Journal of medicinal chemistry* 54.14 (2011): 4937-4953.

Kiselev, Evgeny, et al. "7-azaindenoisoquinolines as topoisomerase I inhibitors and potential anticancer agents." *Journal of medicinal chemistry* 54.17 (2011): 6106-6116.

Kiselev, Evgeny, et al. "Azaindenoisoquinolines as Topoisomerase I Inhibitors and Potential Anticancer Agents: A Systematic Study of Structure—Activity Relationships." *Journal of medicinal chemistry* 55.4 (2012): 1682-1697.

Ruchelman, Alexander L., et al. "5H-Dibenzo[c,h]1,6-naphthyridin-6-ones: novel topoisomerase I-Targeting anticancer agents with potent cytotoxic activity." Bioorganic & medicinal chemistry 11.9 (2003): 2061-2073.

Redinbo, Matthew R., et al. "Crystal structures of human topoisomerase I in covalent and noncovalent complexes with DNA." Science 279.5356 (1998): 1504-1513.

International Search Report for PCT/US2011/048138, dated Jan. 27, 2012.

Hostettman et al., Preparative Chromatography Techniques. Applications in Natural Products Isolation. Springer-Varlag New York 1988, chapter 5 and chapter 10.

Zunino et al., Current status and perspectives in the development of camptothecins. Curr. Pharm.Des. 2002, 8, 2505-2520.

Pommier, Y. Eukaryotic DNA topoisomerase I: Genome gatekeeper and its intruders, camptothecins. Seminars in Oncology 1996, 23, 3-10.

Wang, J. C. DNA Topoisomerases. Annu. Rev. Biochem. 1996, 65, 635-692.

Koster, D. A.; Croquette, V.; Dekker, C; Shuman, S.; Dekker, N. H. Friction and Torque Govern the Relaxation of DNA Supercoils by Eukaryotic Topoisomerase IB. Nature 2005, 434, 671-674.

Stewart, L.; Redinbo, M. R.; Qiu, X.; Hoi, W. G. J.; Champoux, J. J. A Model for the Mechanism of Human Topoisomerase I. Science 1998, 279, 1534-1541.

Wall, M. E.; Wani, M. C; Cook, C. E.; Palmer, K. H.; McPhail, A. T.; Sim, G. A. Plant Antitumor Agents. I. The Isolation and Structure of Camptothecin, a Novel Alkaloidal Leukemia and Tumor Inhibitor from Camptotheca acuminata. J. Am. Chem. Soc. 1966, 88, 3888-3890.

Pommier, E. Topoisomerase I Inhibitors: Camptothecins and Beyond. Nat. Rev. Cancer 2006, 6, 789-802.

Cushman, M.; Cheng, L. Stereo selective Oxidation by Thionyl Chloride Leading to the Indeno[1,2-c]isoquinoline System. J. Org. Chem. 1978, 43, 3781-3783.

Pommier, Y.; Cushman, M. The Indenoisoquinoline Noncamptothecin Topoisomerase I Inhibitors: Update and Perspectives. Mol. Cancer Ther. 2009, 8, 1008-1014.

Morrell, A.; Placzek, M.; Parmley, S.; Grella, B.; Antony, S.; Pommier, Y.; Cushman, M. Optimization of the Indenone Ring of Indenoisoquinoline Topoisomerase I Inhibitors. J. Med. Chem. 2007, 50, 4388-4404.

Morrell, A.; Placzek, M.; Parmley, S.; Antony, S.; Dexheimer, T. S.; Pommier, Y.; Cushman, M. Nitrated Indenoisoquinolines as Topoisomerase I Inhibitors: A Systematic Study and Optimization. J. Med. Chem. 2007, 50, 4419-4430.

Nagarajan, M.; Morrell, A.; Ioanoviciu, A.; Antony, S.; Kohlhagen, G.; Agama, K.; Hollingshead, M.; Pommier, Y.; Cushman, M. Synthesis and Evaluation of Indenoisoquinoline Topoisomerase I Inhibitors Substituted with Nitrogen Heterocycles. J. Med. Chem. 2006, 49, 6283-6289.

Morrell, A.; Placzek, M. S.; Steffen, J. D.; Antony, S.; Agama, K.; Pommier, Y.; Cushman, M. Investigation of the Lactam Side Chain Length Necessary for Optimal Indenoisoquinoline Topoisomerase I Inhibition and Cytotoxicity in Human Cancer Cell Cultures. J. Med. Chem. 2007, 50, 2040-2048.

Li, T. K.; Houghton, P. J.; Desai, S. D.; Daroui, P.; Liu, A. A.; Hars, E. S.; Ruchelman, A. L.; LaVoie, E. J.; Liu, L. F. Characterization of

(56) References Cited

OTHER PUBLICATIONS

ARC-111 As a Novel Topoisomerase I-Targeting Anticancer Drug. Cancer Res. 2003, 63, 8400-8407.

Stadbauer, W.; Kappe, T. Synthesis of Indoles and Isoquinolones from Phenylmalonate Heterocycles. Monatsh. Chem. 1984, 115, 467-475.

Mrkvicka, V.; Klasek, A.; Kimmel, R.; Pevec, A.; Kosmrlj, J. Thermal Reaction of 3aH,5H-Thiazolo[5,4-c]quinoline-2,4-diones—an Easy Pathway to 4-Amino-IH- quinolin-2-ones and Novel 6H-Thiazolo[3,4-c]quinazoline-3,5-Diones. ARKIVOC (Gainsville, FL, United States) 2008, 14, 289-302.

Chong, P. Y.; Janicki, S. Z.; Petillo, P. A. Multilevel Selectivity in the Mild and High-Yielding Chlorosilane-Induced Cleavage of Carbamates to Isocyanates. J. Org. Chem. 1998, 63, 8515-8521.

Potts, K. T.; Robinson, R. Synthetical Experiments Related to Indole Alkaloids. J. Chem. Soc. 1955, 2675-2686.

Johnson, F. Allylic Strain in Six-Membered Rings. Chem. Rev. 1968, 68, 375-413.

Johnson, F. Steric Interference in Allylic and Pseudoallylic Systems. I. Two Stereochemical Theorems. J. Am. Chem. Soc. 1965, 87, 5492-5493.

Xiao, X.; Cushman, M. A Facile Method to Transform trans-4-Carboxy-3,4-dihydro-3-phenyl-I(2H)-isoquinolones to Indeno[1,2-c]isoquinolines. J. Org. Chem. 2005, 70, 6496-6498.

Morrell, A.; Antony, S.; Kohlhagen, G.; Pommier, Y.; Cushman, M. Synthesis of Benz[d]indeno[1,2-b]pyran-5,11-diones: Versatile Intermediates for the Design and Synthesis of.

Verdonk, M. L.; Cole, J. C; Hartshorn, M. J.; Murray, C. W.; Taylor, R. D. Improved ProteinLigand Docking Using GOLD. Protein Struct. Funct. Genet. 2003, 52, 609-623.

Maier, M. E.; Schoeffling, B. Intramolecular Cycloadditions of Mesoionic Carbonyl Ylides with Alkynes. Chem. Ber. 1989, 122, 1081-1087.

Boyd, M. R.; Paull, K. D. Some Practical Considerations and Applications of the National Cancer Institute in Vitro Anticancer Drug Discovery Screen. Drug Development Res. 1995, 34, 91-109.

Pourquier, P.; Ueng, L.-M.; Fertala, J.; Wang, D.; Park, H.-J.; Essigmann, J. M.; Bjornsti, M.-A.; Pommier, Y. Induction of Reversible Complexes between Eukaryotic Dna Topoisomerase I and Dna-containing Oxidative Base Damages. 7,8-Dihydro-8-Oxoguanine and 5-Hydroxycytosine. J. Biol. Chem. 1999, 274, 8516-8523.

* cited by examiner

SUBSTITUTED DIBENZONAPHTHYRIDINES, PHARMACEUTICAL USES THEREOF AND PROCESSES THERFOR

This application is a national stage entry under 35 USC §371(b) of International Application No. PCT/US2011/048138, filed Sep. 2, 2011, which claims priority under 35 U.S.C. §119(e) to U.S. Provisional Application Ser. No. 61/374,430, filed Aug. 17, 2010, which are incorporated herein by reference in their entirety.

GOVERNMENT RIGHTS

This invention was made with government support under U01 CA89566 awarded by the National Institutes of Health. The government has certain rights in the invention.

TECHNICAL FIELD

The invention described herein pertains to substituted dibenzonaphthyridine compounds, pharmaceutical compositions, and formulations comprising the dibenzonaphthyridine compounds, their synthesis, and methods for their use in the treatment and/or prevention of cancer.

BACKGROUND AND SUMMARY OF THE INVENTION

Cells of all living organisms possess topoisomerases to resolve the topological problems associated with DNA supercoiling during various cellular processes (e.g. replication, transcription, repair).[1] There are two major families of topoisomerases: type I and type II. Topisomerase type I (Top1) relaxes both positively and negatively supercoiled DNA via reversible single-strand nicks.[2] Top1 forms a covalent link with the 3'-oxygen atom of DNA.[3] The free 5'-end is then allowed to rotate about the intact strand, thus relieving tension. Once supercoils are removed, the broken DNA strand is re-ligated and the Top1 released.[4] The importance of Top1 for DNA replication and cell division has made it an attractive drug target for anticancer therapy.[5, 6] Camptothecin (CPT, 1), a natural product isolated from the Chinese tree *Camptotheca acuminata*, was the first small molecule to be identified as a Top1 inhibitor (Compound List 1). Topotecan and irinotecan, two clinically relevant analogues of CPT, have previously been described, along with other indenoisoquinolines,[12-19] including an indenoisoquinoline discovered during the total synthesis of nitidine chloride.[7, 8] Interest in indenoisoquinolines was increased by the observation that, despite displaying a similar cytotoxicity profile and ability to inhibit Top1 to that of CPT, the indenoisoquinolines lack the reportedly metabolically unstable lactone ring present in camptothecins.[9, 10] The synthetic Top1 inhibitor topovale (6) has also been previously reported[21]. Cocrystallization of an indenoisoquinoline with Top1-DNA cleavage complex followed by X-ray crystallographic studies of the co-crystals was used to support the proposed molecular mechanism of Top1 inhibition by indenoisoquinolines.[20] Without being bound by theory, it is believed that these molecules function by stabilizing the covalent Top1-DNA cleavage complex and preventing the re-ligation step. Prevention of the re-ligation step reportedly results in enhanced formation of persistent DNA breaks that eventually result in cell death.[11]

Described herein are dibenzonaphthyridine compounds. In one illustrative embodiment, these compounds are dibenzo[c,h][1,6]naphthyridines. In another embodiment, these compounds posses a naphthyridinedione structure. In another illustrative embodiment, the compounds herein are dibenzo[c,h][1,6]naphthyridinediones and chlorodibenzo[c,h][1,6]naphthyridinones. It has been discovered that compounds described herein possess Top1 inhibiting properties. In addition, it has been discovered that compounds described herein are cytotoxic. In another embodiment, compounds are described herein that possess Top1 inhibitory activities with low micromolar to submicromolar cytotoxicity $GI_{50}$ values. In another embodiment, this Top1 inhibition by the compounds herein leads to cell death. In another embodiment, compounds are described herein that possess different or unique DNA cleavage site selectivities compared to CPT and/or indenoisoquinolines. In another embodiment, compounds are described herein that exhibit potent antitumor activities in cancer cell lines. In another embodiment, compounds are described herein that exhibit antiproliferative properties. It is to be understood that the compounds and compositions disclosed herein can be used to control the growth of non-cancer cells that are over proliferating. In another embodiment, described herein are synthetic processes for preparation of the dibenzonaphthyridine compounds. In one aspect, these synthetic routes are efficient and scalable. In another aspect, the synthetic processes described herein may be used for the introduction of a variety of chemically sensitive functional groups into the naphthyridinedione structure. In another embodiment, described herein are pharmaceutical compositions and formulations comprising the dibenzonaphthyridine compounds. In another embodiment, described herein are methods for the use of the dibenzonaphthyridine compounds in the treatment and/or prevention of cancer.

DETAILED DESCRIPTION

In one embodiment, described herein is a compound of the formula

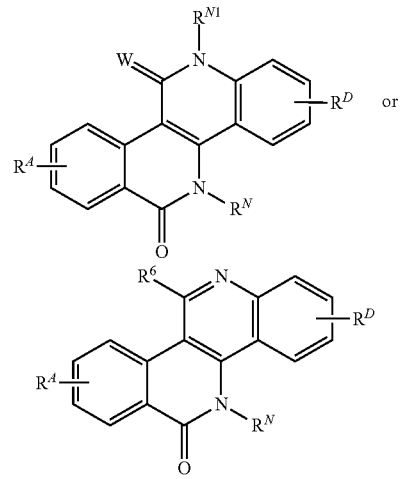

or a pharmaceutically acceptable salt thereof, wherein:

$R^6$ is halo, hydroxy or a derivative thereof, thio, or a derivative thereof, or amino or a derivative thereof, or $R^6$ is alkyl, cycloalkyl, heteroalkyl, cycloheteroalkyl, aryl, heteroaryl, arylalkyl, or heteroarylalkyl, each of which is optionally substituted;

$R^N$ is hydrogen, or alkyl, cycloalkyl, heteroalkyl, heterocyclyl, aryl, arylalkyl, heteroaryl, or heteroarylalkyl, each of which is optionally substituted, or $R^N$ and the attached nitrogen form an amide, carbamate, or urea, or a thiono derivative of the amide, carbamate, or urea; or $R^N$ and the attached nitrogen form an amine prodrug;

$R^{N1}$ is hydrogen, or alkyl, cycloalkyl, heteroalkyl, heterocyclyl, aryl, arylalkyl, heteroaryl, or heteroarylalkyl, each of which is optionally substituted; or $R^N$ and the attached nitrogen form an amide, carbamate, or urea, or a thiono derivative of the amide, carbamate, or urea; or $R^N$ and the attached nitrogen form an amine prodrug;

$R^A$ and $R^D$ each represent 4 substituents, each independently selected from the group consisting of hydrogen, halo, hydroxy and derivatives thereof, amino and derivatives thereof, thio and derivatives thereof, carboxylate and derivatives thereof, sulfinyl and derivatives thereof, sulfonyl and derivatives thereof, phosphinyl and derivatives thereof, and phosphonyl and derivatives thereof, and alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted; and W is O or S.

In another embodiment, described herein is the compound above wherein $R^N$ is selected from the group consisting of hydrogen, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, and optionally substituted acyl.

In another embodiment, described herein is the compound above wherein $R^N$ is $(CH_2)_n—Z^a$, where n is an integer from 1-6, and $Z^a$ is selected from halo, hydroxy, alkoxy, cycloalkoxy, haloalkoxy, halocycloalkoxy, optionally substituted aryloxy, optionally substituted heteroaryloxy, acyloxy, amino, alkyl and dialkylamino, trialkylammonium, hydroxyalkylamino, hydroxyalkylaminoalkylamino, acylamino, hydroxyamino, alkoxylamino, acyloxylamino, cycloalkyl, heteroaryl, halocycloalkyl, alkenyl, alkynyl, acyl, cyano, nitro, azido, thio, alkylsulfonyl, carboxylic acid and derivatives thereof, sulfonic acid and derivatives thereof, and phosphonic acid and derivatives thereof.

In another embodiment, described herein is the compound above wherein $Z^a$ is dialkylamino, including dimethylamino, azido, poly(hydroxyalkyl)amino, hydroxyalkylaminoalkylamino, polyhydroxyalkylaminoalkylamino, hydroxyalkyl (alkylamino), heteroaryl. or a combination thereof.

In another embodiment, described herein is the compound above wherein $Z^a$ is a radical selected from the group of formulae consisting of

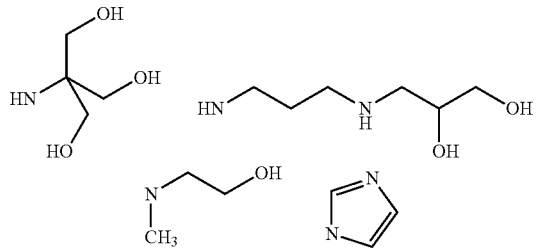

each of which may be optionally substituted.

In another embodiment, described herein is any one of the compounds described above wherein $Z^a$ is a radical having the formula

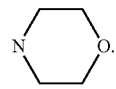

In another embodiment, described herein is the compound above wherein n is 2, 3, or 4.

In another embodiment, described herein is the compound above wherein $R^N$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, hydroxyalkyl(alkylamino), heterocycloalkyl, or combinations thereof.

In another embodiment, described herein is the compound above wherein $R^N$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, hydroxyalkyl(alkylamino), or combinations thereof.

In another embodiment, described herein is the compound above wherein $R^N$ is substituted $C_1$-$C_4$ alkyl.

In another embodiment, described herein is the compound above wherein $R^N$ is optionally substituted heteroalkyl.

In another embodiment, described herein is the compound above wherein $R^N$ is substituted $C_3$ alkyl.

In another embodiment, described herein is the compound above wherein $R^{N1}$ is hydrogen.

In another embodiment, described herein is the compound above wherein $R^A$ and $R^D$ each represent 4 substituents, each independently selected from the group consisting of hydrogen, halo, hydroxy, amino, thio, carboxylate and derivatives thereof, sulfinyl and derivatives thereof, sulfonyl and derivatives thereof, phosphinyl and derivatives thereof, and phosphonyl and derivatives thereof, and alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted.

In another embodiment, described herein is the compound above wherein $R^A$ represents four substituents each independently selected from the group consisting of hydrogen, and a radical $(CH_2)_m Z$, where m is an integer from 0-6 and Z is selected from the group consisting of halo, OH, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, $NH_2$, $C_1$-$C_6$ alkylamino, $(C_1$-$C_6$ alkyl)($C_1$-$C_6$ alkyl)amino, alkylcarbonylamino, N—$(C_1$-$C_6$ alkyl)alkylcarbonylamino, aminoalkyl, $C_1$-$C_6$ alkylaminoalkyl, $(C_1$-$C_6$ alkyl)($C_1$-$C_6$ alkyl)aminoalkyl, alkylcarbonylaminoalkyl, N—$(C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2 R^4$, $CONR^4 R^5$, $P(O)(OR^4)_2$, $P(O)(NR^4 R^5)_2$, and $P(O)(NR^4 R^5)(OR^4)$, where $R^4$ and $R^5$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is the compound above wherein $R^A$ represents four substituents each independently selected from the group consisting of hydrogen and a radical $(CH_2)_m Z$, where m is an integer from 0-6 and Z is selected from the group consisting of halo, OH, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, $NH_2$, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^4R^5$, $P(O)(OR^4)_2$, $P(O)(NR^4R^5)_2$, and $P(O)(NR^4R^5)(OR^4)$, where $R^4$ and $R^5$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is the compound above wherein $R^A$ represents four substituents where two of said substituents are adjacent substituents and are taken together with the attached carbons to form an optionally substituted heterocycle, and the remaining two substituents are each independently selected from the group consisting of hydrogen and a radical $(CH_2)_mZ$, where m is an integer from 0-6 and Z is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^4R^5$, $P(O)(OR^4)_2$, $P(O)(NR^4R^5)_2$, and $P(O)(NR^4R^5)(OR^4)$, where $R^4$ and $R^5$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is the compound above wherein $R^A$ represents four substituents each independently selected from the group consisting of hydrogen, halo, OH, optionally substituted alkyl, optionally substituted alkoxy, cyano, nitro, optionally substituted alkylthio, optionally substituted alkylsulfonyl, $CO_2H$ and derivatives thereof, and $SO_3H$ and derivatives thereof.

In another embodiment, described herein is the compound above wherein $R^A$ represents four substituents where two of said substituents are adjacent substituents and are taken together with the attached carbons to form an optionally substituted heterocycle, and where the two remaining substituents are each independently selected from the group consisting of hydrogen, halo, OH, optionally substituted alkyl, optionally substituted alkoxy, cyano, nitro, optionally substituted alkylthio, optionally substituted alkylsulfonyl, $CO_2H$ and derivatives thereof, and $SO_3H$ and derivatives thereof;

In another embodiment, described herein is the compound above wherein one or more $R^A$ is selected from the group consisting of haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof;

In another embodiment, described herein is the compound above wherein $R^A$ is selected from the group consisting of haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof;

In another embodiment, described herein is the compound above wherein $R^A$ includes two substituents selected from the group consisting of halo, hydroxy, nitro, and optionally substituted alkoxy.

In another embodiment, described herein is the compound above wherein $R^A$ represents a fused optionally substituted heterocycle.

In another embodiment, described herein is the compound above wherein the heterocycle is a 1,3-dioxolane or a 1,4-dioxane.

In another embodiment, described herein is the compound above wherein $R^A$ is bismethoxy or methylenedioxy.

In another embodiment, described herein is the compound above wherein $R^A$ represents four substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^A$ represents at least two adjacent substituents that are taken together with the attached carbons to form an optionally substituted heterocycle.

In another embodiment, described herein is the compound above wherein $R^D$ represents four substituents each independently selected from the group consisting of hydrogen, and a radical $(CH_2)_mZ$, where m is an integer from 0-6 and Z is selected from the group consisting of halo, OH, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, $NH_2$, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^4R^5$, $P(O)(OR^4)_2$, $P(O)(NR^4R^5)_2$, and $P(O)(NR^4R^5)(OR^4)$, where $R^4$ and $R^5$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is the compound above wherein $R^D$ represents four substituents each independently selected from consisting of hydrogen and a radical $(CH_2)_mZ$, where m is an integer from 0-6 and Z is selected from the group consisting of halo, OH, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, $NH_2$, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^4R^5$, $P(O)(OR^4)_2$, $P(O)(NR^4R^5)_2$, and $P(O)(NR^4R^5)(OR^4)$, where $R^4$ and $R^5$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or In another embodiment, described herein is the compound above wherein $R^D$ represents four substituents where two of said substituents are adjacent substituents and are taken together with the attached carbons to form an optionally substituted heterocycle, and the remaining two substituents are each independently selected from the group consisting of hydrogen and a radical $(CH_2)_mZ$, where m is an integer from 0-6 and Z is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^4R^5$, $P(O)(OR^4)_2$, $P(O)(NR^4R^5)_2$, and $P(O)(NR^4R^5)(OR^4)$, where $R^4$ and $R^5$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is the compound above wherein $R^D$ represents four substituents each independently selected from the group consisting of hydrogen, halo, OH, optionally substituted alkyl, optionally substituted alkoxy, cyano, nitro, optionally substituted alkylthio, optionally substituted alkylsulfonyl, $CO_2H$ and derivatives thereof, and $SO_3H$ and derivatives thereof.

In another embodiment, described herein is the compound above wherein $R^D$ represents four substituents where two of said substituents are adjacent substituents and are taken together with the attached carbons to form an optionally substituted heterocycle, and where the two remaining substituents are each independently selected from the group consisting of hydrogen, halo, OH, optionally substituted alkyl, optionally substituted alkoxy, cyano, nitro, optionally substituted alkylthio, optionally substituted alkylsulfonyl, $CO_2H$ and derivatives thereof, and $SO_3H$ and derivatives thereof;

In another embodiment, described herein is the compound above wherein $R^D$ includes two substituents selected from the group consisting of halo, hydroxy, nitro, and optionally substituted alkoxy.

In another embodiment, described herein is the compound above wherein $R^D$ represents a fused optionally substituted heterocycle.

In another embodiment, described herein is the compound above wherein the heterocycle is a 1,3-dioxolane or a 1,4-dioxane.

In another embodiment, described herein is the compound above wherein $R^D$ is bismethoxy or methylenedioxy.

In another embodiment, described herein is the compound above wherein $R^D$ represents four substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^D$ represents at least two adjacent substituents that are taken together with the attached carbons to form an optionally substituted heterocycle.

In another embodiment, described herein is the compound above wherein $R^A$ or $R^D$, or both $R^A$ and $R^D$ includes hydroxy or a derivative thereof selected from the group consisting of OH, alkoxy, alkylsulfoxy, arylsulfoxy, and arylalkylsulfoxy. In another embodiment, described herein is the compound above wherein at least one of $R^A$ or $R^D$ is OH, alkoxy, alkylsulfoxy, arylsulfoxy, or arylalkylsulfoxy.

In another embodiment, described herein is the compound above wherein $R^A$ or $R^D$, or both $R^A$ and $R^D$ includes amino or a derivative thereof selected from the group consisting of $NH_2$, alkylamino, dialkylamino, acylamino, and sulfonylamino, where alkyl is independently selected in each instance In another embodiment, described herein is the compound above wherein at least one of $R^A$ or $R^D$ is $NH_2$, alkylamino, dialkylamino, acylamino, or sulfonylamino, where alkyl is independently selected in each instance.

In another embodiment, described herein is the compound above wherein $R^A$ or $R^D$, or both $R^A$ and $R^D$ includes thio or a derivative thereof selected from the group consisting of SH, and alkylthio. In another embodiment, described herein is the compound above wherein at least one of $R^A$ or $R^D$ is SH or alkylthio.

In another embodiment, described herein is the compound above wherein $R^A$ or $R^D$, or both $R^A$ and $R^D$ includes sulfonyl selected from the group consisting of alkylsulfonyl, arylsulfonyl, and arylalkylsulfonyl. In another embodiment, described herein is the compound above wherein at least one of $R^A$ or $R^D$ is alkylsulfonyl, arylsulfonyl, or arylalkylsulfonyl.

In another embodiment, described herein is the compound above wherein $R^A$ or $R^D$, or both $R^A$ and $R^D$ includes phosphonyl selected from the group consisting of alkylphosphonyl, arylphosphonyl, and arylalkylphosphonyl. In another embodiment, described herein is the compound above wherein at least one of $R^A$ or $R^D$ is alkylphosphonyl, arylphosphonyl, or arylalkylphosphonyl.

In another embodiment, described herein is the compound above wherein $R^A$ or $R^D$, or both $R^A$ and $R^D$ includes $CO_2H$ or a derivative thereof selected from the group consisting of CN, $CO_2M$, where M is a pharmaceutically acceptable cation, an ester, and an amide. In another embodiment, described herein is the compound above wherein at least one of $R^A$ or $R^D$ is CN or $CO_2M$, where M is a pharmaceutically acceptable cation, or $CO_2M$ is an ester or an amide In another embodiment, described herein is the compound above wherein two of $R^A$ are taken to form 2,3-bismethoxy; and two of $R^D$ are taken to form 8,9-methylenedioxy.

In another embodiment, described herein is the compound above wherein $R^A$ includes 2,3-bismethoxy; and $R^D$ includes 8,9-methylenedioxy.

In another embodiment, described herein is the compound above wherein $R^A$ includes a plurality of methoxy groups.

In another embodiment, described herein is the compound above wherein $R^A$ is a plurality of methoxy groups.

In another embodiment, described herein is the compound above wherein $R^D$ includes a plurality of methoxy groups.

In another embodiment, described herein is the compound above wherein $R^D$ is a plurality of methoxy groups.

In another embodiment, described herein is the compound above wherein $R^A$ includes 2,3-bis methoxy, or two of $R^A$ and their attached atoms form 2,3-methylendioxy.

In another embodiment, described herein is the compound above wherein $R^A$ is 2,3-bis methoxy, or 2,3-methylendioxy.

In another embodiment, described herein is the compound above wherein $R^D$ includes 2,3-bis methoxy, or two of $R^D$ and their attached atoms form 2,3-methylendioxy.

In another embodiment, described herein is the compound above wherein $R^D$ is 2,3-bis methoxy, or 2,3-methylendioxy.

In another embodiment, described herein is the compound above wherein $R^N$ is hydroxyalkyl, hydroxyalkoxy, hydroxyaminoalkyl, aminoalkyl, aminoalkoxy, aminoalkylaminoalkyl, heterocyclylalkyl, heterocyclylalkoxy, heterocyclylalkylaminoalkyl, heteroarylalkyl, heteroarylalkoxy, heteroarylalkylaminoalkyl, each of which is optionally substituted.

In another embodiment, described herein is the compound above wherein $R^N$ is heterocyclylalkyl, heterocyclylalkoxy, heterocyclylalkylaminoalkyl, heteroarylalkyl, heteroarylalkoxy, heteroarylalkylaminoalkyl, each of which is optionally substituted, where each heterocyclyl or heteroaryl includes at least one nitrogen.

In another embodiment, described herein is the compound above wherein $R^6$ is halo, or alkoxy or alkylthio, each of which is optionally substituted.

In another embodiment, described herein is the compound above wherein $R^6$ is halo, hydroxy or a derivative thereof, thio or a derivative thereof, or amino or a derivative thereof. In another embodiment, described herein is the compound above wherein $R^6$ is halo.

In another embodiment, described herein is the compound above wherein W is O.

In another embodiment, described herein is a pharmaceutical composition comprising a therapeutically effective amount of one or more of the compounds described herein for treating a cancer. In one illustrative embodiment, the cancer is selected from the group consisting of leukemia, melanoma, and cancers of the lung, colon, CNS, breast, ovary, prostate and kidney. In another illustrative embodiment, the compositions above further comprise one or more carriers, diluents, or excipients, or a combination thereof.

In another embodiment, described herein is a method for treating a cancer, the method comprising the step of administering to a patient in need of relief from the cancer a composition comprising a therapeutically effective amount of one or more of the compounds described herein. In another embodiment of said method, the composition further comprises one or more carriers, diluents, or excipients, or a combination thereof. In one illustrative embodiment of said method, the cancer is selected from the group consisting of leukemia, melanoma, and cancers of the lung, colon, CNS, breast, ovary, prostate and kidney.

In another embodiment, described herein is a process for preparing the compounds herein, the process comprising the step of:

a) reacting a 2-(methoxycarbonylamino)benzaldehyde with an amine to give the corresponding imine; and/or b) reacting said imine with a homophthalic anhydride to give the corresponding 3-[2-(methoxycarbonylamino)phenyl]-4-carboxy-3,4-dihydro-1(2H)-isoquinolone; and/or c) esterifying the carboxy group of said 4-carboxy-3,4-dihydro-1(2H)-isoquinolone to a corresponding 4-alkoxycarbonyl-3,4-dihydro-1(2H)-isoquinolone; and/or d) reacting said 4-alkoxycarbonyl-3,4-dihydro-1(2H)-isoquinolone with sodium hexamethyldisilazide and phenylselenyl chloride to give the corresponding selenide followed by oxidation of said selenide with hydrogen peroxide to give the corresponding alkyl 3-(2-(methoxycarbonylamino)phenyl)-1-oxo-1,2-dihydroisoquinoline-4-carboxylate; and/or e) hydrolysis of said alkyl 3-(2-(methoxycarbonylamino)phenyl)-1-oxo-1,2-dihydroisoquinoline-4-carboxylate with a base to give the corresponding dibenzo[c,h][1,6]naphthyridine-6,11(5H,12H)-dione.

In another embodiment, described herein is a process for preparing the compound herein, wherein the compound is of the formula

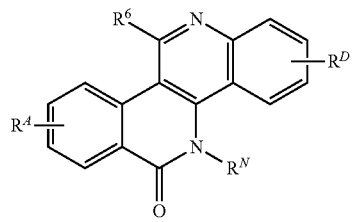

the process comprising the step of:

a) chlorinating a dibenzo[c,h][1,6]naphthyridine-6,11(5H,12H)-dione with a chlorinating reagent comprising $POCl_3$ to give the corresponding 11-chlorodibenzo[c,h][1,6]-naphthyridin-6(5H)-one; and/or b) displacing the chlorine of said 11-chlorodibenzo[c,h][1,6]-naphthyridin-6(5H)-one with a nucleophile.

In another embodiment, described herein is a composition comprising one or more of the compounds described above, and optionally one or more carriers, diluents, or excipients, or a combination thereof.

In another embodiment, described herein is a method for treating a disease responsive to inhibition of topoisomerase 1, the method comprising the step of administering one or more of the compounds or the compositions described above to a patient having the disease. In one embodiment, the disease is a cancer. In another embodiment, the disease is caused by proliferating cells that are not cancer cells. In one illustrative embodiment, the cancer is selected from the group consisting of leukemia, melanoma, and cancers of the lung, colon, CNS, breast, ovary, prostate and kidney. In another illustrative embodiment, the composition above further comprises one or more carriers, diluents, or excipients, or a combination thereof.

It is to be understood that, as used herein, the terms herein, illustratively "dibenzonaphthyridine," "naphthyridinedione," "dibenzonaphthyridinone," "dibenzo[c,h][1,6]naphthyridine," "dibenzo[c,h][1,6]naphthyridinedione," "dibenzo[c,h][1,6]naphthyridinone," as well as the various embodiments represented by the formulae described herein, generally refer to the parent compounds as well as pharmaceutically acceptable salts thereof, including acid and/or base addition salts. In addition, the terms and representative formulae include hydrates and solvates thereof. In addition, the terms and representative formulae include all morphological forms of the compound, including amorphous forms as well as any particular crystal morphology or mixture thereof. In addition, it is to be understood that various prodrugs of the compounds are contemplated herein.

In another embodiment, described herein are pharmaceutical compositions comprising one or more of the compounds herein. The compounds described herein and pharmaceutical compositions comprising them are useful in the treatment of diseases such as cancer.

In another embodiment, described herein are methods of use of the compounds described herein and the pharmaceutical compositions comprising them for treating diseases such as cancer. Illustratively, these methods include administering to a patient in need of relief from the disease a therapeutically effective amount of one or more of the compounds or pharmaceutical compositions described herein. In one aspect, the methods described herein include co-therapies with other therapeutic agents known in the art. Accordingly, the compounds, compositions, formulations and methods described herein may be combined with any one or more of the known compounds or agents known in the art. Accordingly, the co-therapy includes the co-administration of one or more of the compounds or pharmaceutical compositions described herein and one or more of the known compounds or agents known in the art.

It is to be understood that in each of the embodiments described herein, the physical state of the compounds may be amorphous, or in any of a variety of morphological forms. In addition, it is to be understood that the compounds described herein may each be included in the compositions and methods described herein as any number of a variety of pharmaceutical salt forms, or as a hydrate or other solvate.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that alkyl is advantageously of limited length, including $C_1$-$C_{24}$, $C_1$-$C_{12}$, $C_1$-$C_8$, $C_1$-$C_6$, and $C_1$-$C_4$. It is to be further understood that alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior.

As used herein, the term "cycloalkyl" includes a chain of carbon atoms, which is optionally branched, where at least a portion of the chain is cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain is cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl (carbaryl+heteroaryl), or arylalkyl, each of which is optionally substituted.

As used herein, the term "phosphonyl or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH acyloxy, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

Illustrative substituents include, but are not limited to, a radical —$(CH_2)_xZ^x$, where x is an integer from 0-6 and $Z^x$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^x$ is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$) alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$) alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a co-therapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

The following examples further illustrate specific embodiments of the invention; however, the following illustrative examples should not be interpreted in any way to limit the invention.

EXAMPLES

Preparation of the dibenzo[c,h][1,6]naphthyridine-6,11(5H,12H)-diones

Neither of the two previously reported protocols for preparation of dibenzo[c,h][1,6]naphthyridine-6,11(5H,12H)-diones[22, 23] was suitable for the preparation of the compounds described herein. A novel synthetic process was established herein in order to prepare several naphthyridinediones with varying substituent attached to the isoquinolinone lactam. The synthesis of N-methyl derivative 14 is outlined in Scheme 1. The N-protected o-aminobenzaldehyde 7, prepared in two steps from commercially available o-aminobenzylalcohol,[24] was converted to imine 8 by treatment with a methanolic solution of methylamine. The less soluble cis-10 was isolated by filtration of the reaction mixture derived from Schiff base 8 and 4,5-dimethoxyhomophthalic anhydride (9).[25] The trans isomer, trans-10, was obtained by evaporation of the filtrate and recrystallization of the crude product. It is believed that the lower yield of cis-10 relative to its trans analogue may be attributed to the presence of the bulky carbamate in the ortho position. Without being bound by theory, this may also explain the nearly complete isomerization within 24 hours of cis to trans configuration that was observed in an NMR sample of cis-10 dissolved in DMSO-$d_6$. The mixture of both cis- and trans-10 was esterified, producing the more stable trans ester 11. The chemical shifts and coupling constants of H-3 and H-4 were used to establish the cis/trans relationships for acid 10 and ester 11. In the case of cis-10, H-3 and H-4 appear as doublets with coupling constants of 6.6 Hz, whereas in the $^1$H NMR spectrum trans-10, they appear as singlets, consistent with pseudodiaxial substituents at C-3 and C-4 in trans-10, and a pseudoaxial phenyl substituent and pseudoequatorial carboxylic acid in cis-10. In both diastereomers, the C-3 phenyl substituent is pseudoaxial. It is believed that this orientation of the C-3 phenyl substituent may be due to a steric A-strain interaction with the N-methyl group.[26-28] The enolate formed after treatment of 11 with sodium hexamethyldisilazide (NaHMDS) was quenched with phenylselenyl chloride. Oxidation of the resulting phenylselenide with hydrogen peroxide resulted in dehydrogenated product 12. A similar strategy was previously reported for conversion of trans-isoquinolonic acids and esters into indenoisoquinolines.[28] Unexpectedly, the hydrolysis of ester 12 in the presence of potassium hydroxide, followed by acidification with acetic acid, provided the desired product 14 rather than the carboxylic acid 13.

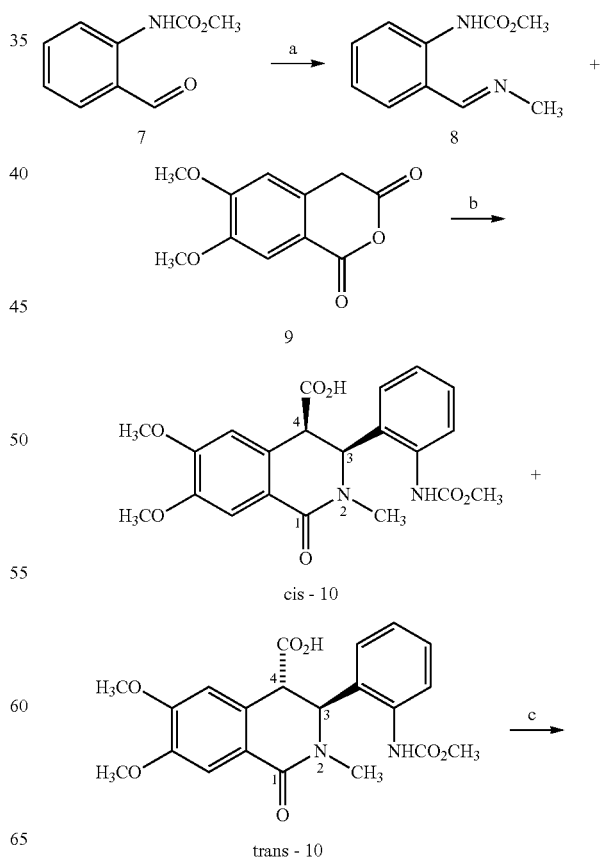

Scheme 1. Synthesis of Dibenzo[c,h][1,6]naphthyridinedione 14[a]

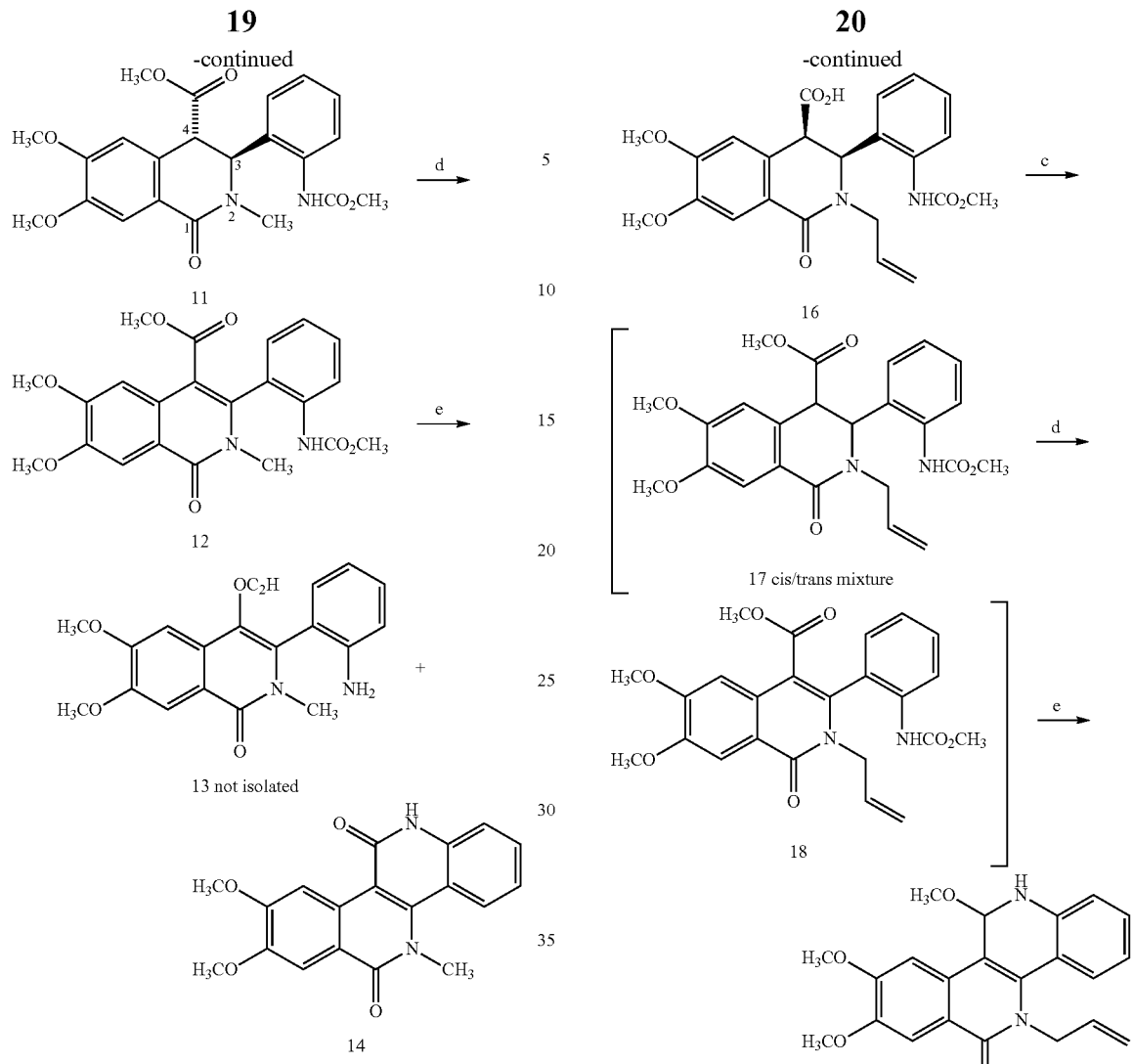

<sup>a</sup>Reagents and conditions: (a) CH₃NH₂, MgSO₄, CH₃OH, room temperature, 6 h (99%); (b) CHCl₃, room temperature, 2 h (cis-10 35%, trans-10 60%; (c) SOCl₂, CH₃OH, 0° C., 6 h (96%); (d) (1) NaHMDS, THF, then PhSeCl, -78° C. to room temperature, 6 h, (2) H₂O₂, CH₃CO₂H, 0° C. to room temperature, 6 h (62%); (e) KOH, water-ethylene glycol (1:1), reflux, 4 d (83%).

In order to prepare a variety of analogues, a method allowing introduction of hydroxy- and aminoalkyl chains in place of the lactam methyl group of the original lead compound 2 was required. Synthesis of the allyl analogue of 14, a potential precursor for optionally substituted alkyl groups attached to the lactam nitrogen, was accomplished in a similar fashion to that described in Scheme 2. Isoquinolonic acid 16 was esterified to 17. The esterification of 16 was accompanied by only partial isomerization of the cis isomer and resulted in a cis/trans mixture 17. Dehydrogenation followed by saponification and cyclization yielded naphthyridinedione 19.

Scheme 2. Synthesis of Allyl Derivative 19<sup>a</sup>

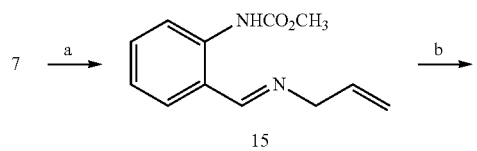

<sup>a</sup>Reagents and conditions: (a) H₂C=CHCH₂NH₂, MgSO₄, CHCl₃, room temperature, 12 h (99%); (b) 9, CHCl₃, room temperature, 18 h (26%); (c) SOCl₂, CH₃OH, 0° C. to room temperature, 6 h; (d) (1) NaHMDS, THF, then PhSeCl, -78° C. to room temperature, overnight, (2) H₂O₂, CH₃CO₂H, 0° C. to room temperature, overnight; (e) KOH, water/ethylene glycol (1:3), reflux, 12 h (43%) over three steps).

The allyl group proved to be stable enough to allow completion of the synthesis of 19. However, further derivatization of the allyl group was difficult to perform. It is believed that the low solubility of the dibenzonaphthyridine 19 contributed to the difficulties encountered in during attempted derivatization of the allyl group.

Syntheses of hydroxypropyl- and two different aminopropyldibenzonaphthyridinediones are shown in Scheme 3. Starting from the O-TBDMS-protected Schiff base 20, the hydroxypropyl analogue 28 was prepared. A similar process was used to convert bromide 21 into N-aminopropyl derivatives 29 and 30. Condensation of 20 or 21 with anhydride 9 produced cis-isoquinolonic acids 22 and 23 (Scheme 3), respectively. The N-3-bromopropyl and N-TBDMSO-propyl interfered with the use of the NaHMDS/phenylselenyl chloride/hydrogen peroxide sequence of steps for the dehydrogenation of the dihydroisoquinolone moieties of 22 and 23. It was previously reported that dehydrogenation of the dihydroisoquinoline fragment could be performed easily on cis-substrates whereas trans-analogues remain unresponsive to the treatment with oxidants like DDQ, CAN, and SeO$_2$.[7, 8] Without being bound by theory, it is suggested that this is due to the observation that in the cis diastereomers, the C-4 proton is likely in a pseudoaxial orientation, resulting in potential overlap of the C—H bond with the neighboring π-system of the aromatic ring, thus facilitating deprotonation.[28] Consequently, a process allowing retention of cis stereochemistry during esterification of 22 and 23 was developed. The near-complete retention of cis configuration was achieved by means of esterification with trimethylsilyldiazomethane at low temperatures. The presence of small amounts of the trans isomers of 24 and 25 was confirmed by NMR spectroscopy of the crude products. In order to avoid further loss or isomerization of the cis-24 and cis-25 during column chromatography or storage, the unpurified mixtures of cis- and trans-esters resulting from the esterification reaction were used in the dehydrogenation step with DDQ. NMR analysis of the products revealed the presence of unchanged trans-24 and trans-25, along with the desired compounds 26 and 27. Treatment of 26 with potassium hydroxide at high temperature, followed by acidification with acetic acid, yielded the cyclized and deprotected N-hydroxypropyldibenzonaphthyridine 28. Reaction of 27 with morpholine or imidazole in hot DMF provided 29 or 30, respectively. The resulting dibenzonaphthyridines were isolated as solids. The more soluble by-products of the reactions remained in solution.

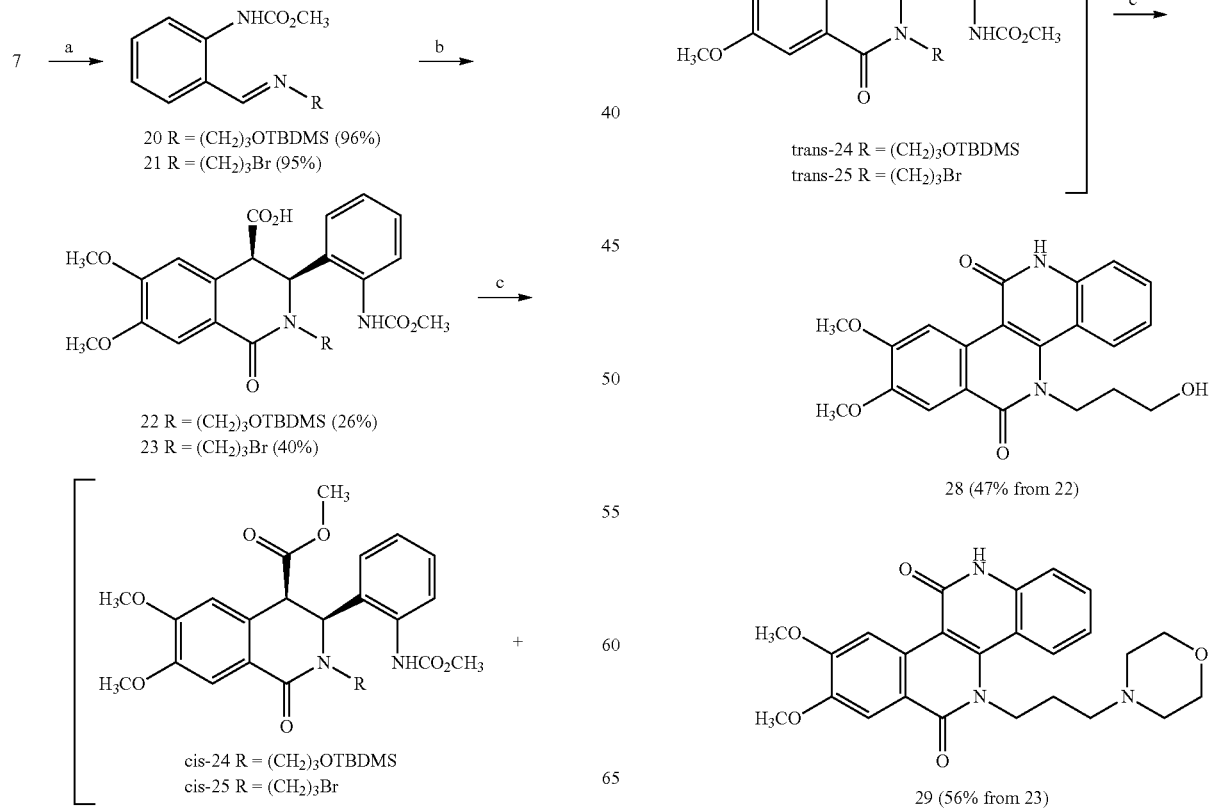

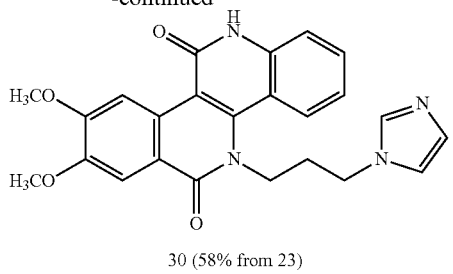

30 (58% from 23)

<sup>a</sup>Reagents and conditions: (a) RNH$_2$, MgSO$_4$, CHCl$_3$, room temperature, 12-24 h; (b) 9, CHCl$_3$, room temperature, 16-18 h; (c) TMSCHN$_2$, CH$_3$OH/THF (1:3), -10 to 0° C., 30-45 min; (d) DDQ (2.2 equiv), 1,4-dioxane, reflux, 3-4 h; (e) KOH, water/ethylene glycol (1:3), reflux for 24 h for 28, or morpholine, DMF, reflux 18 h for 29, or imidazole, DMF, reflux 18-20 h for 30.

Modification of the naphthyridinedione system to provide a variety of substitution patterns is described herein. Naphthyridinediones 14 and 29 were reacted with phosphorus(V) oxychloride (POCl$_3$) or a mixture of POCl$_3$ and PCl$_5$ to yield chloronaphthyridinones 31 and 32, respectively (Scheme 4).

Scheme 4. Synthesis of Chloronaphthyridinones<sup>a</sup>

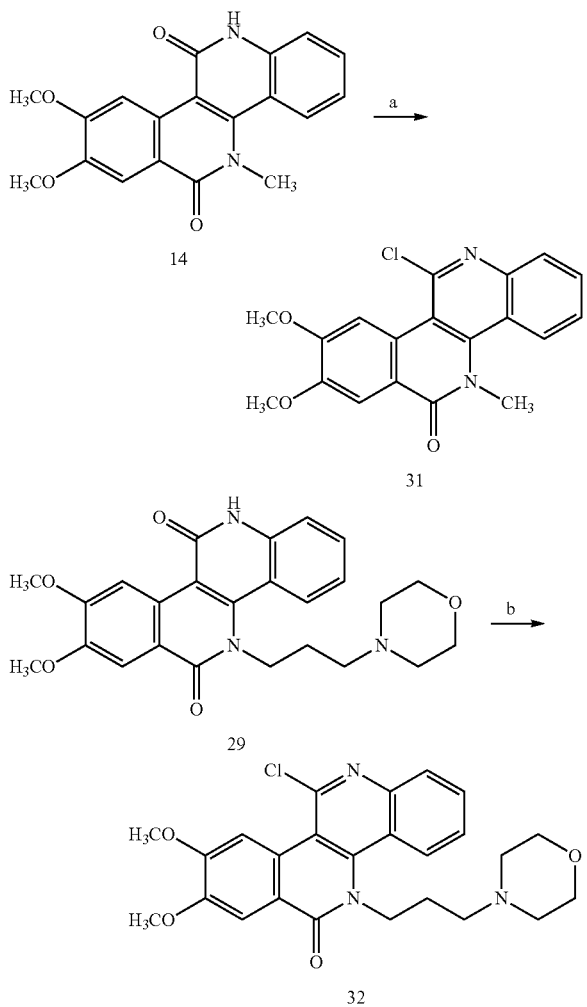

<sup>a</sup>Reagents and conditions: (a) POCl$_3$, DMF, room temperature to 70° C., 7 h (61%); (b) POCl$_3$, PCl$_5$, room temperature, 1 h, reflux 1.5 h (66%).

Heating a solution of 14 in POCl$_3$ for 6 to 12 hours yielded dichloride 33 as the major product (Scheme 5). Both chlorines were subsequently substituted with methoxy groups by reaction with sodium methoxide providing tetramethoxydibenzonaphthyridine 34.

Scheme 5. Synthesis of Naphthridines<sup>a</sup>

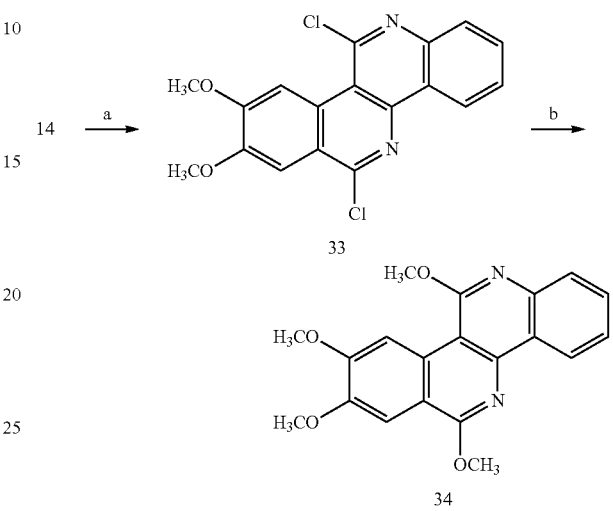

<sup>a</sup>Reagents and conditions: (a) POCl$_3$, PCl$_5$, reflux 6 h (96%); (b) CH$_3$ONa, CH$_3$OH, reflux, 10 h (71%).

Compound Examples

General. Melting points were determined using capillary tubes with a MeI-Temp apparatus and are uncorrected. The proton nuclear magnetic resonance ($^1$H and $^{13}$C NMR) spectra were recorded using an ARX300 300 MHz and DRX500 500 MHz Bruker NMR spectrometers. IR spectra were recorded using a Perkin-Elmer 1600 series FTIR spectrometer. Purity of all tested compounds was ≥95%, as established by combustion analysis. Combustion microanalyses were performed at the Purdue University Microanalysis Laboratory and the reported values were within 0.4% of the calculated values. Analytical thin-layer chromatography was carried out on Baker-flex silica gel IB2-F plates and compounds were visualized with short wavelength UV light. Silica gel flash chromatography was performed using 230-400 mesh silica gel.

Example

Methyl 2-[(Methylimino)methyl]phenylcarbamate (8). A solution of methylamine in methanol (2 N, 3.6 mL, 7.2 mmol) and magnesium sulfate (3 g) were added to 7 (1 g, 5.6 mmol), and mixture was stirred for 6 h. Then precipitate was filtered off and washed with chloroform (3×20 mL). The combined filtrate was concentrated on a rotary evaporator to afford pale-yellow oil (1.08 g, 99%). IR (film) 1733, 1640 cm$^{-1}$; $^1$H NMR (500 MHz, CDCl$_3$) δ 12.18 (s, 1 H), 8.41 (d, J=8.4 Hz, 1 H), 8.28 (d, J=1.0 Hz, 1 H), 7.41-7.33 (m, 1 H), 7.30-7.24 (m, 1 H), 7.08-6.99 (m, 1 H), 3.77 (s, 3 H), 3.50 (d, J=1.3 Hz, 3 H); $^{13}$C NMR (126 MHz, CDCl$_3$) δ 165.57, 154.76, 140.29, 132.99, 131.32, 121.52, 120.46, 118.05, 52.12, 47.96; EIHRMS m/z M$^+$ calcd. for C$_{10}$H$_{12}$N$_2$O$_2$, 192.0899; found, 192.0897.

Example cis-3-[2-(Methoxycarbonylamino)phenyl]-4-carboxy-3,4-dihydro-6,7-dimethoxy-2-methyl-1(2H)-isoquinolone (10). 4,5-Dimethoxyhomophthalic anhydride (9, 1.16 g, 5.2 mmol) was added to a solution of 8 (1 g, 5.2 mmol) in chloroform (10 mL) and the mixture was stirred for 2 h at room temperature. The precipitate was filtered, washed with chloroform (2×10 mL) and dried to yield acid cis 10 (750 mg, 35%): mp 212-213° C. (dec). IR (KBr) 1737, 1626, 1599, 1578 cm$^{-1}$; $^1$H NMR (300 MHz, methanol-$d_4$) δ 7.80 (s, 1 H), 7.51 (s, 1 H), 7.29 (m, 2 H), 7.11 (t, J=7.0 Hz, 1 H), 6.83 (m, 2 H), 5.33 (d, J=6.60 Hz, 1 H), 4.45 (d, J=6.60 Hz, 1 H), 3.80 (s, 3 H), 3.74 (s, 3 H), 3.65 (s, 3 H), 2.80 (s, 3 H); ESIMS m/z (rel intensity) 851 (35), 459 (13), 436 (100), 415 (6), 215 (15); ESIHRMS m/z MNa$^+$ calcd. for $C_{21}H_{22}N_2O_7$, 437.1325; found, 437.1333.

The combined filtrates were evaporated to dryness and the remaining solid was recrystallized from benzene to provide trans 10 (1.3 g, 60%): mp 148-150° C. (dec). IR (KBr) 1730, 1716, 1640 cm$^{-1}$; $^1$H NMR (500 MHz, DMSO-$d_6$) δ 12.91 (s, 1 H), 9.18 (s, 1 H), 7.46 (s, 1 H), 7.36 (s, 1 H), 7.29 (d, J=7.7 Hz, 1 H), 7.23 (t, J=7.5 Hz, 1 H), 7.05 (t, J=7.5 Hz, 1 H), 6.71 (s, 1 H), 6.63 (d, J=7.8 Hz, 1 H), 5.58 (s, 1 H), 3.81 (s, 3 H), 3.80 (s, 1 H), 3.71 (s, 3 H), 3.69 (s, 3 H), 2.88 (s, 3 H); $^{13}$C NMR (126 MHz, DMSO-$d_6$) δ 172.38, 163.02, 155.44, 151.52, 148.23, 135.30, 134.59, 128.34, 128.18, 126.55, 126.25, 125.40, 121.11, 112.12, 109.24, 58.18, 55.63, 55.45, 51.98, 47.78, 33.82.

Example trans-3-[2-(Methoxycarbonylamino)phenyl]-3,4-dihydro-6,7-dimethoxy-4-methoxycarbonyl-2-methyl-1(2H)-isoquinolone (11). Thionyl chloride (10 mL) was added slowly to a suspension of cis 10 (0.75 g, 1.8 mmol) and trans 10 (1.35 g, 3.3 mmol) in methanol (100 mL) at 0° C. The resulting mixture was stirred for 6 h at 0° C. After completion of the reaction (TLC), the reaction mixture was poured slowly into a mixture of ice (200 g) and a saturated solution of sodium bicarbonate (100 mL). The resulting mixture was extracted with chloroform (3×150 mL), and the combined extracts were dried with sodium sulfate, filtered though a thin pad of silica gel, and evaporated to dryness to obtain 11 as amorphous glassy solid (2.1 g, 96%). IR (film) 1733, 1637 cm$^{-1}$; $^1$H NMR (500 MHz, CDCl$_3$) δ 7.67 (s, 1 H), 7.52 (d, J=7.7 Hz, 1 H), 7.25 (t, J=7.0 Hz, 1 H), 7.03 (t, J=7.5 Hz, 1 H), 6.83 (d, J=7.8 Hz, 1 H), 6.73 (s, 1 H), 6.54 (s, 1 H), 5.45 (s, 1 H), 3.95 (s, 3 H), 3.89 (s, 1 H), 3.82 (s, 3 H), 3.72 (s, 3 H), 3.63 (s, 1 H), 3.03 (s, 3 H); $^{13}$C NMR (126 MHz, CDCl$_3$) δ 172.06, 164.17, 155.49, 152.15, 149.18, 134.39, 132.53, 129.10, 126.67, 126.53, 125.93, 125.14, 121.60, 111.86, 110.17, 59.32, 56.29, 56.20, 53.27, 53.06, 48.66, 34.57; ESIMS m/z (rel intensity) 429 (MH$^+$, 100), 451 (56); ESIHRMS m/z MH$^+$ calcd. for $C_{22}H_{24}N_2O_7$, 429.1662; found, 429.1665.

Example

Methyl 6,7-Dimethoxy-3-(2-(methoxycarbonylamino) phenyl)-2-methyl-1-oxo-1,2-dihydroisoquinoline-4-carboxylate (12). NaHMDS (1 M solution in THF-heptanes, 1.8 mL, 1.8 mmol) was slowly added to a solution of 11 (320 mg, 0.75 mmol) in dry THF (20 mL) at −78° C. The reaction mixture was stirred at −78° C. for 1 h, and then a solution of phenylselenyl chloride (216 g, 1.13 mmol) in dry THF (5 mL) was added dropwise and the mixture was stirred at −78° C. for 2 h. The reaction mixture was allowed to warm to room temperature and stirred at this temperature for 3 h. The reaction mixture was quenched by slow addition of 1N HCl (5 mL) at 0° C., diluted with water (50 mL) and extracted with chloroform (4×50 mL). The combined extracts were washed with water and brine, dried with sodium sulfate, and evaporated under reduced pressure. The residue was dissolved in THF (10 mL). Acetic acid (1 mL) and hydrogen peroxide (30%, 5 mL) were added sequentially at 0° C. The reaction mixture was warmed to room temperature and stirred for 6 h. Saturated aqueous sodium bicarbonate (5 mL) was added to the mixture at 0° C. Chloroform (3×10 mL) was used to extract the product. The combined extracts were washed with water and brine, dried with sodium sulfate, and evaporated to afford the product (198 mg, 62%): mp 165-170° C. IR (film) 1730, 1718, 1638 cm$^{-1}$; $^1$H NMR (500 MHz, CDCl$_3$) δ 8.05 (d, J=6.2 Hz, 1 H), 7.86 (s, 1 H), 7.49 (t, J=7.9 Hz, 1 H), 7.22-7.16 (m, 2 H), 7.16-7.11 (m, 1 H), 6.53 (s, 1 H), 4.04 (s, 3 H), 3.99 (s, 3 H), 3.72 (s, 3 H), 3.45 (s, 3 H), 3.24 (s, 3 H); $^{13}$C NMR (126 MHz, CDCl$_3$) δ 167.39, 162.03, 154.22, 154.07, 150.14, 139.65, 136.41, 130.97, 129.29, 128.59, 124.49, 119.35, 112.69, 108.14, 104.80, 56.52, 56.37, 52.75, 52.26, 33.18; ESIMS m/z (rel intensity) 449 (18), 427 (MH$^+$, 100), 395 (78); ESIHRMS m/z MH$^+$ calcd. for $C_{22}H_{22}N_2O_7$, 427,1505; found, 427.1507.

Example 8,9-Dimethoxy-5-methyldibenzo[c,h][1,6]naphthyridine-6,11(5H,12H)-dione (14). The methyl ester 12 (160 mg, 0.38 mmol) was added to a stirred solution of KOH (1.04 g, 18.5 mmol) in water-ethylene glycol mixture (15:15 mL), and the resulting mixture was heated to reflux for 4 d. After the mixture was cooled to room temperature, it was diluted with water (20 mL) and acidified with acetic acid (2.5 mL) and extracted with chloroform (3×100 mL), the combined extracts were washed with water (50 mL), brine (50 mL), dried with sodium sulfate, and evaporated to obtain white powder (105 mg, 83%): mp>350° C. IR (KBr) 1710, 1670, 1651 cm$^{-1}$; $^1$H NMR (500 MHz, DMSO-$d_6$) δ 11.86 (s, 1 H), 9.41 (s, 1 H), 8.18 (d, J=8.30 Hz, 1 H), 7.72 (s, 1 H), 7.55 (t, J=7.20 Hz, 1H), 7.44 (d, J=8.30 Hz, 1 H), 3.92 (s, 3 H), 3.91 (s, 3 H), 3.86 (s, 3 H); positive ESIMS m/z (rel intensity) 374 (60), 337 (MH$^+$, 19), 318 (100); negative ESIMS m/z (rel intensity) 335 ([M-H$^+$], 100). Anal. Calcd for $C_{19}H_{16}N_2O_4$: C, 67.85; H, 4.79; N, 8.33. Found: C, 67.52; H, 4.56; N, 7.97.

Example

Methyl 2-[(Allylimino)methyl]phenylcarbamate (15). Methyl 2-formylphenylcarbamate (7, 1 g, 5.6 mmol) and magnesium sulfate (3 g) were added to a solution of allylamine (1.5 g, 26 mmol) in chloroform (10 mL) and mixture was stirred overnight. Then mixture was filtered and the residue was washed with chloroform (2×10 mL). The combined filtrates were washed with water (3×10 mL) brine (10 mL), dried with sodium sulfate, and concentrated on a rotary evaporator to afford 15 as yellow oil (1.2 g, 99%). IR (film) 1732, 1635 cm$^{-1}$; $^1$H NMR (500 MHz, CDCl$_3$) δ 12.25 (s, 1 H), 8.43 (d, J=8.4 Hz, 1 H), 8.28 (s, 1 H), 7.40-7.34 (m, 1 H), 7.27 (dd, J=7.7, 1.4 Hz, 1 H), 7.02 (td, J=7.5, 0.9 Hz, 1 H), 6.05 (ddt, J=17.1, 10.5, 5.3 Hz, 1 H), 5.25 (ddd, J=17.2, 3.3, 1.6 Hz, 1 H), 5.20-5.13 (m, 1 H), 4.26-4.17 (m, 2 H), 3.76 (s, 3 H); $^{13}$C NMR (126 MHz, CDCl$_3$) δ 164.94, 154.73, 140.38, 135.38, 133.25, 131.54, 121.49, 120.32, 118.05, 115.99, 62.88, 52.10; ESIMS m/z (rel intensity) 219 (MH$^+$, 100); EIHRMS m/z M$^+$ calcd. for $C_{12}H_{14}N_2O_2$, 218.1055; found, 218.1053.

Example cis-2-Allyl-6,7-dimethoxy-3-(2-(methoxycarbonylamino)phenyl)-1-oxo-1,2,3,4-tetrahydroisoquinoline-4-carboxylic Acid (16). 4,5-Dimethoxyhomophthalic anhydride (9, 444 mg, 2 mmol) was added to a solution of 15 (700 mg, 2 mmol) in chloroform (5 mL) and the mixture was stirred at room temperature for 18 h. The precipitate was collected and washed with chloroform (2×20 mL) to obtain a white solid (300 mg, 26%): mp 219-220° C. (dec). IR (KBr) 1746, 1618 cm$^{-1}$; $^1$H NMR (500 MHz, DMSO-d$_6$) δ 12.80 (s, 1 H), 8.79 (s, 1 H), 7.52 (s, 1 H), 7.37 (d, J=7.9 Hz, 1 H), 7.30-7.20 (m, 1 H), 7.12-7.01 (m, 2 H), 6.87 (s, 1 H), 5.72-5.50 (m, 1 H), 5.39 (d, J=5.9 Hz, 1 H), 4.99 (dd, J=10.3, 1.3 Hz, 1 H), 4.91 (dd, J=17.2, 1.5 Hz, 1 H), 4.46-4.36 (m, 2 H), 3.83 (s, 3 H), 3.77 (s, 3 H), 3.63 (s, 3 H), 3.29 (dd, J=15.4, 6.6 Hz, 1 H); $^{13}$C NMR (126 MHz, DMSO-d$_6$) δ 171.54, 164.02, 155.37, 151.91, 148.35, 136.46, 133.58, 131.43, 128.66, 128.30, 128.26, 125.43, 121.80, 117.18, 110.54, 110.25, 55.95, 55.84, 54.54, 52.18, 48.37, 47.13; ESIMS m/z (rel intensity) 479 (MK$^+$, 100), 441 (MH$^+$, 26); ESIHRMS m/z MH$^+$ calcd. for $C_{23}H_{24}N_2O_7$, 441.16662; found, 441.1657.

Example

5-Allyl-8,9-dimethoxydibenzo[c,h][1,6]naphthyridine-6,11(5H,12H)-dione (19). Thionyl chloride (10 mL) was added slowly to a suspension of 16 (990 mg, 2.24 mmol) in methanol (50 mL) at 0° C. The resulting mixture was stirred for 6 h at room temperature. After completion of the reaction, the mixture was poured slowly into ice (200 g) and neutralized with a saturated aqueous sodium bicarbonate solution (100 mL). The organic products were extracted with chloroform (3×50 mL), and the combined extracts were dried with sodium sulfate and concentrated. The solid residue (17, cis/trans mixture) was redissolved in dry THF (30 mL). NaHMDS (1 M solution in THF-heptanes, 5 mL, 5 mmol) was slowly added to the resulting solution. The reaction mixture was stirred at –78° C. for 2 h and then a solution of phenylselenyl chloride (728 mg, 3.1 mmol) in dry THF (10 mL) was added dropwise and the mixture was stirred at –78° C. for additional 2 h. The reaction mixture was allowed to warm to room temperature and stirred at this temperature overnight. The reaction mixture was quenched by slow addition of 1N HCl (55 mL) at 0° C., diluted with water (50 mL) and extracted with chloroform (4×50 mL). The combined extracts were washed with water and brine, dried with sodium sulfate, and evaporated under reduced pressure. The residue was dissolved in THF (50 mL). Acetic acid (5 mL) and hydrogen peroxide (30%, 30 mL) were added sequentially at 0° C. The reaction mixture was warmed to room temperature and stirred overnight. Saturated sodium bicarbonate (15 mL) was added to the mixture at 0° C. The precipitate was collected by filtration, washed with water and hot methanol, providing 18 as white solid mass (118 mg, 15%). The combined filtrates were extracted with chloroform (3×10 mL). The combined extracts were washed with water and brine, dried with sodium sulfate, and evaporated to dryness. The residue was added to a mixture of potassium hydroxide (560 mg, 10 mmol), water (10 mL), and ethylene glycol (30 mL). The resulting solution was heated to reflux for 12 h. After cooling to ambient temperature, acetic acid was added to neutralize the solution. The precipitate was collected by filtration and washed with water and hot methanol providing the rest of 19 (215 mg, 28%, total yield 343 mg, 43%): mp 298-300° C. IR (KBr) 1691, 1602, 1500 cm$^{-1}$; $^1$H NMR (500 MHz, DMSO-d$_6$) δ 11.86 (s, 1 H), 9.38 (s, 1 H), 8.14 (d, J=8.4 Hz, 1 H), 7.69 (s, 1 H), 7.53 (t, J=7.6 Hz, 1 H), 7.43 (d, J=8.2 Hz, 1 H), 7.18 (t, J=7.7 Hz, 1 H), 6.33-6.14 (m, 1 H), 5.31 (d, J=10.7 Hz, 1 H), 5.17 (d, J=17.5 Hz, 1 H), 4.87 (s, 2 H), 3.91 (s, 3 H), 3.90 (s, 3H); $^{13}$C NMR (126 MHz, DMSO-d$_6$) δ 162.69, 161.09, 153.31, 149.53, 144.72, 137.67, 135.41, 130.73, 129.05, 126.25, 121.17, 118.98, 116.65, 116.25, 113.17, 108.21, 107.71, 107.41, 55.93, 55.79, 53.72; ESIMS m/z (rel intensity) 475 (MNa$^+$, 100), 453 (MH$^+$, 18). Anal. Calcd for $C_{21}H_{18}N_2O_4$: C, 69.60; H, 5.01; N, 7.73. Found: C, 69.22; H, 4.88; N, 7.64.

Example

Methyl 2-[(3-Bromopropylimino)methyl]phenylcarbamate (21). Methyl 2-formylphenylcarbamate (7, 2.5 g, 14 mmol) and magnesium sulfate (5 g) were added to a solution of 3-bromopropylamine hydrochloride (3.68 g, 16.8 mmol) and triethylamine in chloroform (30 mL) and mixture was stirred for 24 h. The mixture was filtered and the residue was washed with chloroform (2×30 mL). The combined filtrates were washed with water (2×30 mL), brine (30 mL), dried with sodium sulfate, and concentrated to afford 21 as a yellow oil (3.95 g, 94.5%). IR (film) 1730, 1638 cm$^{-1}$; $^1$H NMR (300 MHz, CDCl$_3$) δ 8.38 (d, J=8.4 Hz, 1 H), 8.30 (s, 1 H), 7.35 (t, J=7.7 Hz, 2 H), 7.26 (d, J=7.7 Hz, 1 H), 7.00 (t, J=7.4 Hz, 1 H), 3.74 (s, 3 H), 3.69 (t, J=6.3 Hz, 2 H), 3.50 (t, J=6.6 Hz, 2 H), 2.20 (pent, J=6.3 Hz, 2 H); $^{13}$C NMR (75 MHz, CDCl$_3$) δ 164.74, 154.30, 140.07, 133.00, 131.32, 121.25, 119.79, 117.69, 58.17, 52.87, 33.16, 31.15; ESIMS m/z (rel intensity) 299/301 (MH$^+$, 100/99); EIHRMS m/z M$^+$ calcd. for $C_{12}H_{15}BrN_2O_2$, 298.0317; found, 298.0320.

Example cis-2-[3-(tert-Butyldimethylsilyloxy)propyl]-6,7-dimethoxy-3-(2-(methoxycarbonylamino)phenyl)-1-oxo-1,2,3,4-tetrahydroisoquinoline-4-carboxylic Acid (22). Methyl 2-formylphenylcarbamate (7, 1.79 g, 10 mmol) and magnesium sulfate (3 g) were added to a solution of 3-(tert-butyldimethylsilyloxy)propan-1-amine (1.89 g, 10 mmol) in chloroform (10 mL) and the mixture was stirred overnight. Then mixture was filtered and the residue was washed with chloroform (2×10 mL). The combined filtrate was concentrated on a rotary evaporator to afford crude 20 as yellow oil (3.37 g, 96%) that was used without additional purification. $^1$H NMR (300 MHz, CDCl$_3$) δ 8.38 (d, J=8.4 Hz, 1 H), 8.30 (s, 1 H), 7.35 (t, J=7.7 Hz, 2 H), 7.26 (d, J=7.7 Hz, 1 H), 7.00 (t, J=7.4 Hz, 1 H), 3.71-3.69 (m, 5 H), 3.60 (m, 2 H), 1.83 (pent, J=6.3 Hz, 2 H), 0.84 (s, 9 H), –0.01 (s, 6 H); ESIMS m/z (rel intensity) 299/301 (MH$^+$, 100/99). 4,5-Dimethoxyhomophthalic anhydride (9, 444 mg, 2 mmol) was added to a solution of 20 (700 mg, 2 mmol) in chloroform (5 mL) and the mixture was stirred at room temperature for 18 h. The precipitate was collected and washed with chloroform (2×20 mL) to obtain a white solid (300 mg, 26%): mp 252-258° C. (dec). IR (KBr) 3357, 1733 cm$^{-1}$; $^1$H NMR (500 MHz, DMSO-d$_6$) δ 8.91 (s, 1 H), 7.50 (s, 1 H), 7.41 (d, J=8.3 Hz, 1 H), 7.28-7.19 (m, 1 H), 7.01 (d, J=6.2 Hz, 2 H), 6.86 (s, 1 H), 5.46 (d, J=5.9 Hz, 1 H), 4.39 (d, J=5.9 Hz, 1 H), 3.85-3.72 (m, 7 H), 3.64 (s, 3 H), 3.52-3.39 (m, 2 H), 2.78 (ddd, J=13.7, 9.1, 5.0 Hz, 1 H), 1.54 (ddd, J=21.7, 13.6, 7.4 Hz, 2 H), 0.78 (s, 9 H), –0.07 (s, 6 H); $^{13}$C NMR (126 MHz, DMSO-d$_6$) δ 171.17, 163.66, 155.01, 151.40, 147.92, 136.25, 128.22, 127.86, 124.82, 121.78, 110.13, 109.91, 60.88, 55.58, 55.49, 54.52, 51.81, 48.07, 42.37, 30.23, 25.79, 17.88, –5.42, –5.45; ESIMS m/z (rel intensity) 573 (MH$^+$, 64), 441 (100); ESIHRMS m/z MH$^+$ calcd. for $C_{29}H_{40}N_2O_8Si$, 573.2632; found, 573.2636.

Example cis-2-(3-Bromopropyl)-6,7-dimethoxy-3-[2-(methoxycarbonylamino)phenyl]-1-oxo-1,2,3,4-tetrahydroisoquinoline-4-carboxylic Acid (23). 4,5-Dimethoxyhomophthalic anhydride (9, 222 mg, 1 mmol) was added to a solution of 21 (300 mg, 10 mmol) in chloroform (5 mL) and the mixture was stirred at room temperature for 16 h. The precipitate was collected and washed with chloroform (2×20 mL) to obtain a white solid (208 mg, 40%): mp 264-266° C. (dec). IR (KBr) 3391, 1726 cm$^{-1}$; $^1$H NMR (500 MHz, DMSO-d$_6$) δ 12.81 (s, 1 H), 8.84 (s, 1 H), 7.52 (s, 1 H), 7.40 (d, J=8.1 Hz, 1 H), 7.30-7.20 (m, 1 H), 7.02 (t, J=7.3 Hz, 1 H), 6.96 (dd, J=7.9, 1.3 Hz, 1 H), 6.86 (s, 1 H), 5.50 (d, J=6.0 Hz, 1 H), 4.51 (d, J=6.0 Hz, 1 H), 3.91-3.79 (m, 4 H), 3.76 (d, J=14.9 Hz, 3 H), 3.66 (d, J=12.4 Hz, 3 H), 3.45-3.37 (m, 2 H), 2.84 (ddd, J=13.6, 8.2, 5.6 Hz, 1 H), 1.96 (ddt, J=21.7, 14.2, 7.0 Hz, 2 H); $^{13}$C NMR (126 MHz, DMSO-d$_6$) δ 171.03, 163.68, 155.04, 151.52, 147.93, 136.30, 128.36, 127.63, 127.56, 125.03, 121.49, 110.05, 109.99, 55.58, 55.50, 54.67, 51.89, 47.82, 44.09, 32.09, 30.63; ESIMS m/z (rel intensity) 299/301 (MH$^+$, 100/99) 543/545 (MNa$^+$, 68/63), 441 (100).

Example 5-(3-Hydroxypropyl)-8,9-dimethoxydibenzo[c,h][1,6]naphthyridine-6,11(5H,12H)-dione (28). Trimethylsilyldiazomethane (0.12 mL, 2.0 M in diethyl ether, 0.25 mmol) was added dropwise to a suspension of 22 (110 mg, 0.19 mmol) in methanol (1 mL) and THF (3 mL) at −10 to 0° C., and the mixture was stirred at −10° C. for 30-45 min after addition. The solvent was removed under reduced pressure at 20-25° C. The residue (24, cis-trans mixture) was dissolved in anhydrous 1,4-dioxane (5 mL) and DDQ (100 mg, 0.44 mmol) was added to the solution. The reaction mixture was heated at reflux for 3-4 h. 1,4-Dioxane was evaporated under reduced pressure and chloroform (30 mL) was added to the residue. The mixture was washed with sodium bicarbonate (5%, 2×10 mL), water (15 mL), dried with sodium sulfate, and filtered through a thin layer of silica gel, eluting with chloroform. The combined filtrates were evaporated under reduced pressure. The amorphous solid containing 26 was added to a stirred solution of KOH (180 mg, 18.5 mmol) in water-ethylene glycol mixture (1+3 mL) at room temperature, and the mixture was heated at reflux on oil bath for 24 h. After the mixture was cooled to room temperature, it was diluted with water (5 mL) and acidified with acetic acid (0.5 mL). The white precipitate was collected by filtration to obtain 28 as a white powder (24 mg, 47%): mp 313° C. IR (KBr) 1650, 1604 cm$^{-1}$; $^1$H NMR (500 MHz, DMSO-d$_6$) δ 11.85 (s, 1 H), 9.36 (s, 1 H), 8.02 (d, J=8.3 Hz, 1 H), 7.71 (s, 1 H), 7.54 (t, J=7.6 Hz, 1 H), 7.44 (d, J=8.1 Hz, 1 H), 7.23 (t, J=7.6 Hz, 1 H), 4.51 (t, J=6.8 Hz, 2 H), 4.43 (t, J=4.8 Hz, 1 H), 3.92 (s, 3 H), 3.91 (s, 3 H), 3.22 (dd, J=10.8, 5.5 Hz, 2 H), 2.05-1.81 (m, 2 H); $^{13}$C NMR (126 MHz, DMSO-d$_6$) δ 162.82, 160.88, 152.96, 149.17, 144.41, 137.37, 130.28, 128.54, 126.19, 121.07, 118.95, 115.89, 113.14, 107.83, 107.40, 57.90, 55.63, 55.50, 48.77, 31.35; positive ESIMS m/z (rel intensity) 381 (MH$^+$, 100). Anal. Calcd for $C_{21}H_{20}N_2O_5$: C, 66.31; H, 5.30; N, 7.36. Found: C, 66.03; H, 5.16; N, 7.26.

Example 8,9-Dimethoxy-5-(3-morpholinopropyl)dibenzo[c,h][1,6]naphthyridine-6,11(5H,12H)-dione (29). Trimethylsilyldiazomethane (0.12 mL, 2.0 M in diethyl ether, 0.25 mmol) was added dropwise to a suspension of 23 (100 mg, 0.19 mmol) in methanol (1 mL) and THF (3 mL) at −10 to 0° C. The mixture was kept in this temperature range for 30 min after addition. The reaction mixture became clear after stirring at 0° C. for 30-45 min. The solvent was removed under reduced pressure at 20-25° C. to yield solid residue 24 that melts at 183-184° C. Without additional purification the residue was dissolved in anhydrous 1,4-dioxane (5 mL) and DDQ (100 mg, 0.44 mmol) was added to the solution. The reaction mixture was heated at reflux for 3-4 h. 1,4-Dioxane was evaporated under reduced pressure and chloroform (30 mL) was added to the residue. The resulting mixture was washed with sodium bicarbonate (5%, 2×10 mL), water (15 mL), dried with sodium sulfate, and filtered through a thin layer of silica gel, eluting with chloroform. The combined filtrates were evaporated under reduced pressure. The residue containing 27 was redissolved in dry DMF (5 mL). Morpholine (200 mg, 2.3 mmol) was added to the solution and the mixture was heated to reflux for 18 h. The mixture was then cooled to room temperature (precipitate started forming prior to cooling). The precipitate was collected by filtration and washed with methanol and diethyl ether on a filter, and the product was dried to yield pure 29 (48 mg, 56%): mp 250-252° C. IR (KBr) 1649, 1603 cm$^{-1}$; $^1$H NMR (500 MHz, DMSO-d$_6$) δ 11.83 (s, 1 H), 9.35 (s, 1 H), 7.94 (d, J=8.3 Hz, 1 H), 7.71 (d, J=2.5 Hz, 1 H), 7.62-7.51 (m, 1 H), 7.44 (dd, J=8.2, 1.1 Hz, 1 H), 7.29-7.14 (m, 1 H), 4.57 (t, J=6.1 Hz, 2 H), 3.91 (s, 3 H), 3.91 (s, 3 H), 3.13 (s, 4 H), 1.94 (s, 4 H), 1.89-1.82 (m, 2 H), 1.79 (d, J=5.6 Hz, 2 H); $^{13}$C NMR (126 MHz, DMSO-d$_6$) δ 162.66, 160.94, 152.99, 149.12, 145.03, 137.34, 130.16, 128.54, 126.05, 120.89, 118.80, 115.78, 113.64, 107.73, 107.42, 107.09, 65.78, 55.61, 55.50, 53.85, 52.65, 48.80; positive ESIMS m/z (rel intensity) 450 (MH$^+$, 92); negative ESIMS m/z (rel intensity) 448 ([M-H$^+$], 100). Anal. Calcd for $C_{25}H_{27}N_3O_5$: C, 66.80; H, 6.05; N, 9.35. Found: C, 66.49; H, 5.73; N, 9.22.

Example 5-(3-(1H-Imidazol-1-yl)propyl)-8,9-dimethoxydibenzo[c,h][1,6]-naphthyridine-6,11(5H,12H)dione (30). Trimethylsilyldiazomethane (0.12 mL) was added dropwise to a suspension of 23 (100 mg, 0.19 mmol) in methanol (1 mL) and THF (3 mL) at −10 to 0° C. The mixture was kept at this temperature for 30 min after addition. The reaction mixture became clear after stirring at 0° C. for 30-45 min. The solvent was removed under reduced pressure at 20-25° C. to yield solid residue 24 that melts at 183-184° C. Without additional purification, the residue was dissolved in anhydrous 1,4-dioxane (5 mL) and DDQ (100 mg, 0.44 mmol) was added to the solution. The reaction mixture was heated at reflux for 3-4 h. 1,4-Dioxane was evaporated under reduced pressure and chloroform (30 mL) was added to the residue. The mixture was washed with aqueous sodium bicarbonate (5%, 2×10 mL), water (15 mL), dried with sodium sulfate, and filtered through a thin layer of silica gel, eluting with chloroform. The combined filtrates were evaporated under reduced pressure. The residue containing 27 was redissolved in dry DMF (5 mL). Imidazole (160 mg, 2.3 mmol) was added to the solution and the mixture was heated to reflux for 18-20 h. The mixture was then cooled to room temperature (precipitate started forming prior to cooling). The precipitate was collected by filtration and washed with methanol and diethyl ether on a filter, and the product was dried to yield pure 30 (47 mg, 58%): mp 288-290° C. IR (KBr) 1659, 1636 1601 cm$^{-1}$; $^1$H NMR (500 MHz, DMSO-d$_6$) δ 11.86 (s, 1 H), 9.36 (s, 1 H), 7.77 (d, J=8.3 Hz, 1 H), 7.71 (s, 1 H), 7.56-7.48 (m, 2 H), 7.42 (d, J=8.2 Hz, 1 H), 7.13 (t, J=7.7 Hz, 1 H), 7.08 (s, 1 H), 6.81

(s, 1 H), 4.40-4.28 (m, 2 H), 3.99-3.91 (m, 5 H), 3.91 (s, 3 H), 2.40-2.23 (m, 2 H); $^{13}$C NMR (126 MHz, DMSO-d$_6$) δ 162.77, 160.78, 153.03, 149.23, 143.94, 137.34, 137.14, 130.29, 128.59, 128.46, 125.56, 121.15, 119.16, 118.82, 115.92, 112.77, 107.86, 107.55, 107.39, 55.63, 55.50, 48.67, 43.54, 29.61; positive ESIMS m/z (rel intensity) 431 (MH$^+$, 100); negative ESIMS m/z (rel intensity) 429 ([M-H$^+$],100); ESIHRMS m/z MH$^+$ calcd. for C$_{24}$H$_{22}$N$_4$O$_4$, 431.1719; found, 431.1120. Anal. Calcd for C$_{24}$H$_{22}$N$_4$O$_4$.0.7H$_2$O: C, 65.06; H, 5.32; N, 12.65. Found: C, 64.98; H, 5.40; N, 12.37.

Example

11-Chloro-8,9-dimethoxy-5-methyldibenzo[c,h][1,6] naphthyridin-6(5H)-one (31). Dry DMF (1 mL) was added slowly to a mixture of 14 (84 mg, 0.25 mmol) and phosphoryl chloride (10 mL) at 0° C. The mixture was allowed to warm up to room temperature. The mixture was heated to 70° C. and kept at 65-70° C. for 2 h. After disappearance of starting material (TLC), the mixture was cooled to 0° C., poured into the ice (50 g), and neutralized with concentrated ammonium hydroxide. The precipitate was collected by filtration and purified by preparative TLC to get an off-white solid (54 mg, 61%): mp 242-243° C. IR (KBr) 1650, 1605 cm$^{-1}$; $^1$H NMR (500 MHz, CDCl$_3$) δ 8.69 (s, 1 H), 8.20 (d, J=8.6 Hz, 1 H), 8.01 (d, J=8.3 Hz, 1 H), 7.94 (s, 1 H), 7.71 (t, J=7.6 Hz, 1 H), 7.54 (t, J=7.7 Hz, 1 H), 4.07 (s, 3 H), 4.06 (s, 3 H), 4.03 (s, 3 H); $^{13}$C NMR (126 MHz, CDCl$_3$) δ 163.12, 152.95, 150.30, 146.61, 145.57, 145.40, 130.36, 128.69, 126.51, 125.75, 124.93, 119.96, 118.71, 111.14, 108.76, 107.97, 56.48, 40.73; positive ESIMS m/z (rel intensity) 355/357 (MH$^+$, 100/33). Anal. Calcd for C$_{19}$H$_{15}$ClN$_2$O$_3$.0.5H$_2$O: C, 62.73; H, 4.43; N, 7.70. Found: C, 62.74; H, 4.75; N, 7.38.

Example

11-Chloro-8,9-dimethoxy-5-(3-morpholinopropyl) dibenzo[c,h][1,6]-naphthyridin-6(5H)-one (32)

Precursor 29 (22.5 mg, 0.05 mmol) was mixed with POCl$_3$ (3 mL) and phosphorus pentachloride (100 mg, 10 equiv) was added slowly at room temperature. Starting material dissolved upon PCl$_5$ addition, forming a clear yellow solution. The reaction mixture was stirred for 1 h and then heated at reflux for 1.5 h. After disappearance of starting material, the reaction mixture was cooled to room temperature and concentrated under reduced pressure. The brown oily residue was dissolved completely in ice-cold water (3 mL) and concentrated ammonium hydroxide solution was added dropwise to neutral pH. The cloudy aqueous solution was extracted with ethyl acetate (3×30 mL). The combined extracts were washed with concentrated ammonium hydrochloride solution, dried with sodium sulfate and evaporated to dryness under reduced pressure to yield 32 as an amorphous solid (15 mg, 66%): mp 185-190° C. (dec.), IR (KBr) 1651, 1606 cm$^{-1}$; $^1$H NMR (500 MHz, CDCl$_3$) δ 8.52 (s, 1 H), 8.17 (d, J=8.5 Hz, 1 H), 7.95 (d, J=7.6 Hz, 1 H), 7.82 (t, J=7.6 Hz, 1 H), 7.77 (s, 1 H), 7.71 (t, J=7.4 Hz, 1 H), 4.56-4.28 (m, 2 H), 3.97 (s, 3 H), 3.96-3.88 (m, 5 H), 3.76 (t, J=12.0 Hz, 2 H), 3.42 (d, J=11.9 Hz, 2 H), 3.18 (s, 2 H), 3.05 (d, J=11.1 Hz, 2 H), 2.42 (s, 2 H); $^{13}$C NMR (126 MHz, CDCl$_3$) δ 161.90, 152.44, 149.88, 145.75, 144.76, 144.57, 130.45, 127.92, 126.50, 125.47, 124.66, 119.34, 117.80, 110.25, 108.06, 107.89, 63.23, 55.91, 55.78, 53.12, 50.89, 48.68, 22.93; positive ESIMS m/z (rel intensity) 468/470 (MH$^+$, 100/32), 381/383 (97/30). Anal. Calcd for C$_{25}$H$_{28}$Cl$_3$N$_3$O$_4$.1.2H$_2$O: C, 53.38; H, 5.45; N, 7.47. Found: C, 53.36; H, 5.45; N, 7.10.

Example 6,11-Dichloro-8,9-dimethoxydibenzo[c,h][1,6]naphthyridine (33). Compound 14 (700 mg, 2.04 mmol) and phosphorus pentachloride (868 mg, 4 mmol) were dissolved in POCl$_3$ (25 mL) at room temperature. The resulting solution was stirred for 2 h, and then heated at reflux for 6 h. The reaction mixture was cooled to room temperature, concentrated to about 5-6 mL, and quenched by pouring slowly into ice (50 g). The mixture was neutralized by adding a concentrated solution of ammonium hydroxide. The precipitate was separated by filtration and washed several times with small portions (5 mL) of ice-cold water providing light-gray powder (690 mg, 96%): mp 245-246° C. IR (KBr) 1655, 1616, 1570, 1559, 1517 cm$^{-1}$; $^1$H NMR (500 MHz, CDCl$_3$) δ 9.23 (s, 1 H), 9.03 (d, J=7.8 Hz, 1 H), 8.06 (d, J=8.1 Hz, 1 H), 7.82 (t, J=7.2 Hz, 1 H), 7.79-7.69 (m, 2 H), 4.15 (s, 3 H), 4.10 (s, 3 H); $^{13}$C NMR (126 MHz, CDCl$_3$) δ 154.73, 153.76, 150.54, 146.72, 146.51, 144.52, 131.02, 129.64, 128.02, 127.96, 124.95, 122.10, 114.65, 106.93, 106.83, 56.67, 56.39; positive ESIMS m/z (rel intensity) 359/360/361 (MH$^+$, 100/22/65). Anal. Calcd for C$_{18}$H$_{12}$Cl$_2$N$_2$O$_2$.0.6H$_2$O: C, 58.43; H, 3.60; N, 7.57. Found: C, 58.32; H, 3.43; N, 7.53.

Example 6,8,9,11-Tetramethoxydibenzo[c,h][1,6]naphthyridine (34). Sodium methoxide (63 mg, 1.17 mmol) and 33 (70 mg, 0.2 mmol) were mixed in methanol (10 mL). The mixture was heated to reflux for 10 h. The reaction mixture was cooled to room temperature and ice-cold water (10 mL) was added. The precipitated white amorphous solid (50 mg, 71%) was collected by filtration: mp 173-175° C. IR (KBr) 1650, 1610, 1590, 1515 cm$^{-1}$; $^1$H NMR (500 MHz, DMSO-d$_6$) δ 8.80 (d, J=7.2 Hz, 1 H), 8.57 (s, 1 H), 7.78 (d, J=7.8 Hz, 1 H), 7.70 (t, J=7.3 Hz, 1 H), 7.59-7.45 (m, 2 H), 4.24 (s, 3 H), 4.19 (s, 3 H), 3.95 (s, 3 H), 3.91 (s, 3 H); $^{13}$C NMR (126 MHz, CDCl$_3$) δ 160.78, 159.51, 153.11, 149.48, 146.29, 143.82, 129.96, 129.49, 126.60, 124.42, 124.34, 123.50, 114.22, 107.61, 105.68, 103.90, 55.82, 55.72, 54.24, 53.95; positive ESIMS m/z (rel intensity) 351 (MH$^+$, 100). Anal. Calcd for C$_{20}$H$_{18}$N$_2$O$_4$.0.6H$_2$O: C, 66.51; H, 5.36; N, 7.76. Found: C, 66.41; H, 5.08; N, 7.54.

Example

Topoisomerase I-Mediated DNA Cleavage Reactions. Human recombinant Top1 was purified from Baculovirus as described previously.[34] The 161 bp fragment from pBluescript SK(-) phagemid DNA (Stratagene, La Jolla, Calif.) was cleaved with the restriction endonucleases PvuII and HindIII (New England Biolabs, Beverly, Mass.) supplied in NE buffer 2 (50 µL reactions) for 1 h at 37° C., and separated by electrophoresis in a 1% agarose gel made in 1×TBE buffer. The 161 bp fragment was eluted from the gel slice using the QIAEX II kit (QIAGEN Inc., Valencia, Calif.). Approximately 200 ng of the fragment was 3'-end labeled at the HindIII site by fill-in reaction with [alpha-$^{32}$P]-dGTP and 0.5 mM dATP, dCTP, and dTTP, in React 2 buffer (50 mM Tris-HCl, pH 8.0, 100 mM MgCl$_2$, 50 mM NaCl) with 0.5 unit of DNA polymerase I (Klenow fragment). Unincorporated $^{32}$P-dGTP was removed using mini Quick Spin DNA columns (Roche, Indianapolis, Ind.), and the eluate containing the 3'-end-labeled 161 bp fragment was collected. Aliquots (approximately 50,000 dpm/reaction) were incubated with topoisomerase I at 22° C. for 30 min in the presence of the tested drug. Reactions were terminated by adding SDS (0.5% final concentration). The samples (10 μL) were mixed with 30 μL of loading buffer (80% formamide, 10 mM sodium hydroxide, 1 mM sodium EDTA, 0.1% xylene cyanol, and 0.1% bromophenol blue, pH 8.0). Aliquots were separated in denaturing gels (16% polyacrylamine, 7 M urea). Gels were dried and visualized by using a Phosphoimager and ImageQuant software (Molecular Dynamics, Sunnyvale, Calif.). Each gel included a sample of DNA alone, DNA with only the drug, and DNA with Top I without the drug. The compounds described herein were tested at concentrations of 0.1 μM, 1 μM, 10 μM, 100 μM. The activity of the compounds to produce Top1-mediated DNA cleavage is expressed semi-quantitatively as follows: +: weak activity; ++ and +++: moderate activity; ++++: similar activity as 1 μM camptothecin. Results: 33, 0; 34, 0; 32, ++; 31, +++; 30, +; 29, +; 28, 0; and 19, 0.

Example

Molecular Modeling. Structures of 36 and 37 were built and geometry optimized with Sybyl 8.1 using the MMFF94s force field and MMFF94 charges.[31] The X-ray crystal structure was obtained from the Protein Data Bank (PDB ID: 1SC7). Hydrogens were added to all atoms and MMFF94 charges were assigned. The positions of hydrogen atoms were optimized with the MMFF94s force field. The original ligand 5 was removed from the structure of the ternary complex,[20] and 100 docking runs were performed for both 36 and 37 using the docking genetic algorithm and Goldscore fitness function within GOLD 3.2.[30] The best solutions were merged with the Top1-DNA cleavage complex. In order to refine the position of the naphthyridine ligands, geometry optimizations of the ligands within newly obtained ternary complexes were performed by 100 iterations with steepest descent minimization followed by 200 iterations with conjugate gradient using the MMFF94s force field and MMFF94 charges within Sybyl 8.1.

Example

Biological Results. All of the target compounds were tested for induction of DNA damage in Top1-mediated DNA cleavage assays. The results of this assay are designated relative to the Top1 inhibitory activity of CPT and expressed in semi-quantitative fashion on the scale from 0, no detectable activity, to ++++, similar activity to that of compound 1 at a concentration of 1 μM. Naphthyridinediones 14, 19, and 28 showed no detectable inhibition of Top1 in this assay. Compounds 29 and 30, containing an N-(3-morpholinylpropyl) or an N-(3-imidazolylpropyl), respectively were Top1 inhibitors, but only at the lower + level. Without being bound by theory, it is believed that the loss of Top1 inhibitory activity with expansion of the five-membered indenone ring of the indenoisoquinoline to the six-membered ring of compounds described herein might result from the decreased overall solubility, especially for 14, 19, and 28, rather than differences in intercalation between DNA base pairs at the Top1 cleavage site. With 29 and 30, incorporation of amines increased water solubility and affinity toward DNA, possibly due to attraction of their positively charged protonated amines with the phosphates of the DNA backbone. The comparison of the naphthyridinedione 30 to indenoisoquinoline 35[29] revealed that despite having similar substituents on the isoquinolinone moiety, the activity of the naphthyridinedione appears to be lower (Compound list 2).

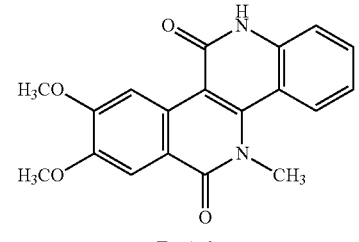

14

Top1: 0

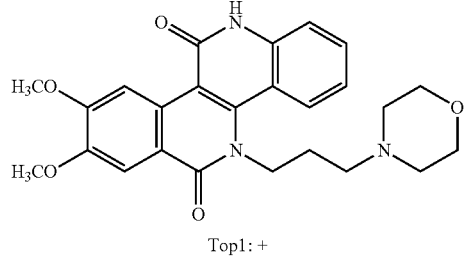

29

Top1: +

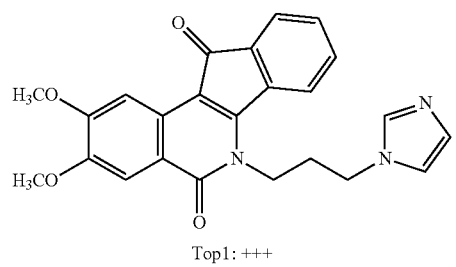

35

Top1: +++

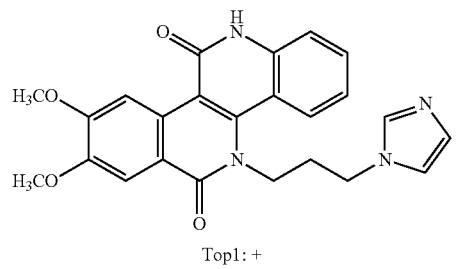

30

Top1: +

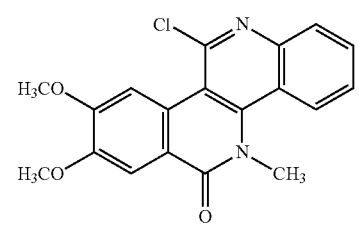

31

Top1: +++

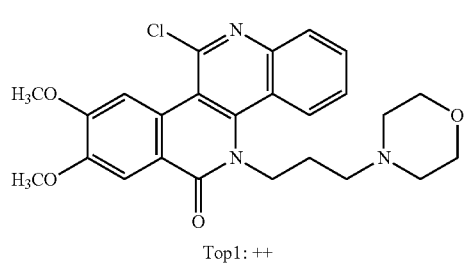

32

Top1: ++

Compound List 2. The relative Top1 inhibitory potencies of the compounds are presented as follows: 0: no detectable activity; +: weak activity; ++: similar activity as compound 2; +++ and ++++: greater activity than compound 2; ++++: similar activity as 1 µM CPT.

After conversion of the quinolinone fragment to a chloroquinoline, the observed Top1 inhibitory activity appears to have increased from 0 for 14 to +++ for 31, and from + for 29 to ++ for 32. The solubilities of 31 and 32 in solvents like DMSO, methanol and chloroform also increased substantially relative to their precursors 14 and 29. Further aromatization of the isoquinolinone moiety appears to have resulted in loss of activity for dichloride 33 and tetramethoxynaphthyridine 34 despite similarity of their polycyclic systems to nitidine chloride (3). In the case of the indenoisoquinolines, it has been reported that Top1 inhibitory activity was increased by replacement of an N-methyl group by a chain of 2-4 carbon atoms with a polar group attached at its end.[17-19]

The Top1-mediated DNA fragmentation patterns produced by camptothecin, indenoisoquinolines 2, 4, and synthesized compounds 19 and 28-34, were compared. Inspection of the cleavage band intensities for compound 31 appears to show that, unlike indenoisoquinolines, the cleavages at base pairs 44 and 68 are weak. However, the band for cleavage at the base pair 97 is more intense. Without being bound by theory, it is believed that the DNA cleavage-site selectivity of chloronaphthyridinone 31 bears greater similarity to the cleavage-site selectivity of camptothecins than to the cleavage-site selectivity indenoisoquinolines. In the case of compound 32, it is difficult to come to a similar conclusion as only bands for cleavages at the 97 and 119 sites are intense enough to be significant. The behavior of 32 is different from the camptothecins, the indenoisoquinolines, and the chlorodibenzonaphthyridinone 31. Without being bound by theory, it is suggested that the dibenzonaphthyridines may offer the opportunity to target the genome differently from either the camptothecins or the indenoisoquinolines.

Despite the fact that a number of structures of different classes of Top1 inhibitors within drug-Top1-DNA ternary complex have been obtained by X-ray crystallography,[20] the binding orientations of 3 and dibenzonaphthyridines like 6 have not been determined. Therefore, hypothetical binding models of naphthyridine-Top1-DNA ternary complexes were constructed in order to better understand the reasons underlying the change of activity in transitioning from indenoisoquinolines to naphthyridinedione and to chloronaphthyridinones. Binding models were constructed by means of docking and molecular mechanics tools. The dibenzonaphthyridine structures were docked using GOLD[30] in place of the ligand of the reported crystal structure of the 5-Top1-DNA ternary complex (PDB ID: 1SC7[20]), and the geometries of the docked structures were optimized using the MMFF94s force field in Sybyl 8.1.[31] The main goal of this molecular modeling was to calculate the preferred binding orientation of the dibenzonaphthyridine polycyclic core. Therefore, the model compounds 36 and 37 that lack the conformationally flexible methoxy groups were used in order to facilitate the docking search process. Both 36 and 37 are oriented with the longer axis of the ligand oriented along the longer axis of the base pair. In the case of 36, the isoquinolinone moiety faces the minor groove of the DNA and the distance of 2.6 Å between isoquinolinone oxygen and a nitrogen of the Arg364 side chain is consistent with a hydrogen bond. The most favorable orientation calculated for 37 is turned almost 180° around the axis perpendicular to the plane of the molecule relative to 36. The chloroquinoline moiety of 37 faces the minor groove with a 2.8 Å distance between quinoline nitrogen and Arg364. Both molecules appear slightly bent out of plane. This bend results in one the benzene rings of 36 being closer to the thymine of the AT base pair, possibly causing disfavorable steric interactions. On the contrary, the bend of 37 nearly perfectly mirrors the out-of-plane distortion of the AT base pair, which may contribute to the better fit and higher Top1 inhibitory activity of this type of inhibitor.

Molecules 14 and 31 possess methoxy groups on the isoquinolinone benzene ring. According to calculated binding orientation of 36, the bulky substituents of 14 would be located on the side of the intact DNA strand causing some additional unfavorable steric interaction with the DNA backbone. On the other hand, the methoxy groups of 31 would be placed toward the less restricted scissile strand in accord with the binding orientation calculated for 37. Without being bound by theory, it is believed herein that the binding orientation might explain the difference in activity between 14 and 31. Further similarities between chlorodibenzonaphthyridinones and 1 are evident from comparison of the experimentally determined binding orientation for 1 and the calculated binding mode of 37, which may indicate that in both cases the quinoline fragment is located on the side of the intact DNA strand with the quinoline nitrogen facing Arg364 in the minor groove. In the case of the hypothetically determined binding mode of 37, the quinoline nitrogen is placed somewhat closer to the Arg364 compared to 1, forcing the polycyclic core of the dibenzonaphthyridinone to move deeper between flanking base pairs within the ternary complex.

The antiproliferative activity of each compound was tested against 55 different human cancer cell lines in the National Cancer Institute screen.[32, 33] The chlorodibenzonaphthyridinone 32 bearing a morpholinopropyl chain on the lactam nitrogen was cytotoxic to human cancer cells at low micromolar concentrations. The cytotoxicities of 32 in selected cell lines are presented in Table 1, along with the mean graph midpoint value of 5.6 µM. In general, cytotoxicity $GI_{50}$ values appeared to be in the low micromolar range, although 32 was particularly cytotoxic in the leukemia K-562 and RPMI-8226 cell lines, the ovarian IGROV1 cancer cell line, the renal UO-31 cancer cell line, and the breast MCF7 cancer cell line.

TABLE 1

Antiproliferative Activity of Dibenzonaphthyridine 32.

| Cancer cell line | $GI_{50}$ (µM)$^a$ |
|---|---|
| Leukemia | |
| K-562 | 0.2 |
| RPMI-8226 | 0.1 |
| Lung | |
| HOP-62 | 4.7 |
| Colon | |
| HCT-116 | 4.16 |
| COLO 205 | 0.33 |
| CNS | |
| SF-539 | 12.3 |
| Melanoma | |
| UACC-62 | 6.8 |
| Ovarian | |
| OVCAR-3 | 6.3 |
| IGROV1 | 0.03 |
| Renal | |
| SN12C | 13.2 |
| UO-31 | 0.02 |

TABLE 1-continued

Antiproliferative Activity of Dibenzonaphthyridine 32.

| Cancer cell line | GI$_{50}$ (μM)[a] |
|---|---|
| Prostate | |
| DU-145 | 10.5 |
| Breast | |
| MCF7 | 0.4 |
| MGM[b] | 5.6 ± 1.3 |

[a]The cytotoxicity GI$_{50}$ values are the concentrations corresponding to 50% growth inhibition.
[b]Mean graph midpoint for growth inhibition of all human cancer cell lines successfully tested. The compound was tested at concentrations ranging up to 10 μM.

The following publications, and each additional publication cited herein, are incorporated herein by reference.

1. Wang, J. C. DNA Topoisomerases. Annu. Rev. Biochem. 1996, 65, 635-692.
2. Koster, D. A.; Croquette, V.; Dekker, C.; Shuman, S.; Dekker, N. H. Friction and Torque Govern the Relaxation of DNA Supercoils by Eukaryotic Topoisomerase IB. Nature 2005, 434, 671-674.
3. Stewart, L.; Redinbo, M. R.; Qiu, X.; Hol, W. G. J.; Champoux, J. J. A Model for the Mechanism of Human Topoisomerase I. Science 1998, 279, 1534-1541.
4. Redinbo, M. R.; Stewart, L.; Kuhn, P.; Champoux, J. J.; Hol, W. G. J. Crystal Structures of Human Topoisomerase I in Covalent and Noncovalent Complexes with DNA. Science 1998, 279, 1504-1513.
5. Wall, M. E.; Wani, M. C.; Cook, C. E.; Palmer, K. H.; McPhail, A. T.; Sim, G. A. Plant Antitumor Agents. I. The Isolation and Structure of Camptothecin, a Novel Alkaloidal Leukemia and Tumor Inhibitor from *Camptotheca acuminata*. J. Am. Chem. Soc. 1966, 88, 3888-3890.
6. Pommier, E. Topoisomerase I Inhibitors: Camptothecins and Beyond. Nat. Rev. Cancer 2006, 6, 789-802.
7. Hostettman, K.; Hostettman, M.; Marston, A. Preparative Chromatography Techniques. Applications in Natural Products Isolation. Springer-Varlag: New York, 1988.
8. Cushman, M.; Cheng, L. Stereoselective Oxidation by Thionyl Chloride Leading to the Indeno[1,2-c]isoquinoline System. J. Org. Chem. 1978, 43, 3781-3783.
9. Kohlhagen, G.; Paull, K.; Cushman, M.; Nagafuji, P.; Pommier, Y. Protein-Linked DNA Strand Breaks Induced by NSC 314622, a Novel Noncamptothecin Topoisomerase I Poison. Mol. Pharmacol. 1998, 54, 50-58.
10. Pommier, Y. Eukaryotic DNA topoisomerase I: Genome gatekeeper and its intruders, camptothecins. Seminars in Oncology 1996, 23, 3-10.
11. Zunino, F.; Dallavalle, S.; Laccabue, D.; Beretta, G.; Merlini, L.; Pratesi, G. Current Satus and Perspectives in the Development of Camptothecins. Curr. Pharm. Des. 2002, 8, 2505-2520.
12. Strumberg, D.; Pommier, Y.; Paull, K.; Jayaraman, M.; Nagafuji, P.; Cushman, M. Synthesis of Cytotoxic Indenoisoquinoline Topoisomerase I Poisons. J. Med. Chem. 1999, 42, 446-457.
13. Cushman, M.; Jayaraman, M.; Vroman, J. A.; Fukunaga, A. K.; Fox, B. M.; Kohlhagen, G.; Strumberg, D.; Pommier, Y. Synthesis of New Indeno[1,2-c]isoquinolines: Cytotoxic Non-Camptothecin Topoisomerase I Inhibitors. J. Med. Chem. 2000, 43, 3688-3698.
14. Pommier, Y.; Cushman, M. The Indenoisoquinoline Noncamptothecin Topoisomerase I Inhibitors: Update and Perspectives. Mol. Cancer. Ther. 2009, 8, 1008-1014.
15. Morrell, A.; Placzek, M.; Parmley, S.; Grella, B.; Antony, S.; Pommier, Y.; Cushman, M. Optimization of the Indenone Ring of Indenoisoquinoline Topoisomerase I Inhibitors. J. Med. Chem. 2007, 50, 4388-4404.
16. Morrell, A.; Placzek, M.; Parmley, S.; Antony, S.; Dexheimer, T. S.; Pommier, Y.; Cushman, M. Nitrated Indenoisoquinolines as Topoisomerase I Inhibitors: A Systematic Study and Optimization. J. Med. Chem. 2007, 50, 4419-4430.
17. Nagarajan, M.; Xiao, X.; Antony, S.; Kohlhagen, G.; Pommier, Y.; Cushman, M. Design, Synthesis, and Biological Evaluation of Indenoisoquinoline Topoisomerase I Inhibitors Featuring Polyamine Side Chains on the Lactam Nitrogen. J. Med. Chem. 2003, 46, 5712-5724.
18. Nagarajan, M.; Morrell, A.; Ioanoviciu, A.; Antony, S.; Kohlhagen, G.; Agama, K.; Hollingshead, M.; Pommier, Y.; Cushman, M. Synthesis and Evaluation of Indenoisoquinoline Topoisomerase I Inhibitors Substituted with Nitrogen Heterocycles. J. Med. Chem. 2006, 49, 6283-6289.
19. Morrell, A.; Placzek, M. S.; Steffen, J. D.; Antony, S.; Agama, K.; Pommier, Y.; Cushman, M. Investigation of the Lactam Side Chain Length Necessary for Optimal Indenoisoquinoline Topoisomerase I Inhibition and Cytotoxicity in Human Cancer Cell Cultures. J. Med. Chem. 2007, 50, 2040-2048.
20. Staker, B. L.; Feese, M. D.; Cushman, M.; Pommier, Y.; Zembower, D.; Stewart, L.; Burgin, A. B. Structures of Three Classes of Anticancer Agents bound to the Human Topoisomerase I-DNA Covalent Complex. J. Med. Chem. 2005, 48, 2336-2345.
21. Li, T. K.; Houghton, P. J.; Desai, S. D.; Daroui, P.; Liu, A. A.; Hars, E. S.; Ruchelman, A. L.; LaVoie, E. J.; Liu, L. F. Characterization of ARC-111 As a Novel Topoisomerase I-Targeting Anticancer Drug. Cancer Res. 2003, 63, 8400-8407.
22. Stadbauer, W.; Kappe, T. Synthesis of Indoles and Isoquinolones from Phenylmalonate Heterocycles. Monatsh. Chem. 1984, 115, 467-475.
23. Mrkvicka, V.; Klasek, A.; Kimmel, R.; Pevec, A.; Kosmrlj, J. Thermal Reaction of 3aH,5H-Thiazolo[5,4-c]quinoline-2,4-diones—an Easy Pathway to 4-Amino-1H-quinolin-2-ones and Novel 6H-Thiazolo[3,4-c]quinazoline-3,5-Diones. ARKIVOC (Gainsville, Fla., United States) 2008, 14, 289-302.
24. Chong, P. Y.; Janicki, S. Z.; Petillo, P. A. Multilevel Selectivity in the Mild and High-Yielding Chlorosilane-Induced Cleavage of Carbamates to Isocyanates. J. Org. Chem. 1998, 63, 8515-8521.
25. Potts, K. T.; Robinson, R. Synthetical Experiments Related to Indole Alkaloids. J. Chem. Soc. 1955, 2675-2686.
26. Johnson, F. Allylic Strain in Six-Membered Rings. Chem. Rev. 1968, 68, 375-413.
27. Johnson, F. Steric Interference in Allylic and Pseudoallylic Systems. I. Two Stereochemical Theorems. J. Am. Chem. Soc. 1965, 87, 5492-5493.
28. Xiao, X.; Cushman, M. A Facile Method to Transform trans-4-Carboxy-3,4-dihydro-3-phenyl-1(2H)-isoquinolones to Indeno[1,2-c]isoquinolines. J. Org. Chem. 2005, 70, 6496-6498.
29. Morrell, A.; Antony, S.; Kohlhagen, G.; Pommier, Y.; Cushman, M. Synthesis of Benz[d]indeno[1,2-b]pyran-5,11-diones: Versatile Intermediates for the Design and Synthesis of Topoisomerase I Inhibitors. Bioorg. Med. Chem. Lett. 2006, 16, 1846-1849.
30. Verdonk, M. L.; Cole, J. C.; Hartshorn, M. J.; Murray, C. W.; Taylor, R. D. Improved Protein-Ligand Docking Using GOLD. Protein Struct. Funct. Genet. 2003, 52, 609-623.
31. SYBYL 7.3, Tripos International: St. Louis.

32. Maier, M. E.; Schoeffling, B. Intramolecular Cycloadditions of Mesoionic Carbonyl Ylides with Alkynes. Chem. Ber. 1989, 122, 1081-1087.

33. Boyd, M. R.; Paull, K. D. Some Practical Considerations and Applications of the National Cancer Institute In Vitro Anticancer Drug Discovery Screen. Drug Development Res. 1995, 34, 91-109.

34. Pourquier, P.; Ueng, L.-M.; Fertala, J.; Wang, D.; Park, H.-J.; Essigmann, J. M.; Bjornsti, M.-A.; Pommier, Y. Induction of Reversible Complexes between Eukaryotic DNA Topoisomerase I and DNA-containing Oxidative Base Damages. 7,8-Dihydro-8-Oxoguanine and 5-Hydroxycytosine. J. Biol. Chem. 1999, 274, 8516-8523.

What is claimed is:

1. A compound of the formula

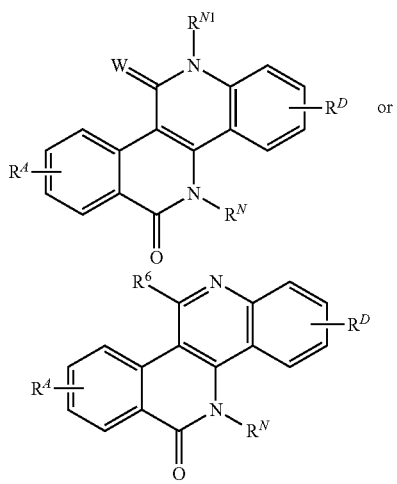

or a pharmaceutically acceptable salt thereof, wherein:
  $R^6$ is halo, hydroxy or a derivative thereof, thio or a derivative thereof, or amino or a derivative thereof;
  $R^N$ is heteroalkyl, heterocyclyl, heterocyclyl-alkyl, arylalkyl, or heteroarylalkyl;
  $R^{N1}$ is hydrogen, heteroalkyl, heterocyclyl, heterocyclyl-alkyl, arylalkyl, or heteroarylalkyl;
  $R^A$ and $R^D$ each represent 4 substituents, each independently selected from the group consisting of hydrogen, hydroxy and derivatives thereof, amino and derivatives thereof, thio and derivatives thereof, and alkyl, alkenyl, alkynyl, cycloalkyl, heteroalkyl, cycloheteroalkyl, cycloheteroalkenyl, aryl, heteroaryl, arylalkyl, and heteroarylalkyl; and
  W is O or S.

2. The compound of claim 1 wherein $R^N$ is selected from the group consisting of arylalkyl and heteroarylalkyl.

3. The compound of claim 1 wherein $R^N$ is $(CH_2)_n-Z^a$, where n is an integer from 1-6, and $Z^a$ is selected from amino, dialkylamino, trialkylammonium, hydroxyalkylamino, hydroxyalkylaminoalkylamino, acylamino, alkoxylamino, acyloxyamino, heteroaryl, and heterocyclyl.

4. The compound of claim 3 wherein $Z^a$ is dimethylamino.

5. The compound of claim 3 wherein $Z^a$ is a radical selected from the group of formulae consisting of

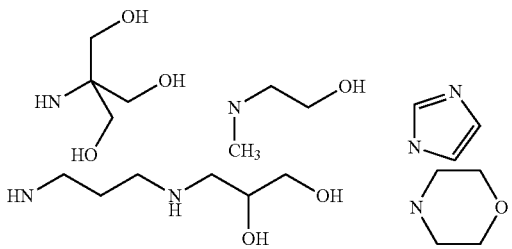

6. The compound of claim 3 wherein n is 2, 3, or 4.

7. The compound of claim 1 wherein $R^A$ represents four substituents each independently selected from the group consisting of hydrogen, OH, alkyl, and alkoxy.

8. The compound of claim 1 wherein $R^A$ represents four substituents each of which is independently selected from the group consisting of hydrogen, alkyl, and alkoxy.

9. The compound of claim 1 wherein $R^D$ represents four substituents each of which is independently selected from the group consisting of hydrogen, alkyl, and alkoxy.

10. The compound of claim 1 wherein $R^A$ includes 8,9-dimethoxy.

11. The compound of claim 1 wherein $R^D$ includes 2,3-dimethoxy.

12. The compound of claim 1 wherein $R^6$ is halo, alkoxy or alkylthio.

13. The compound of claim 1 wherein $R^6$ is halo.

14. The compound of claim 1 wherein W is O.

15. A pharmaceutical composition comprising a therapeutically effective amount of one or more compounds of claim 1 and further comprising one or more carriers, diluents, or excipients, or a combination thereof for treating a cancer.

16. A process for preparing a compound of claim 1, the process comprising the steps of:
  a) reacting a 2-(methoxycarbonylamino)benzaldehyde with an amine to give the corresponding imine;
  b) reacting said imine with a homophthalic anhydride to give the corresponding 3-[2-(methoxycarbonylamino)phenyl]-4-carboxy-3,4-dihydro-1(2H)-isoquinolone;
  c) esterifying the carboxy group of said 4-carboxy-3,4-dihydro-1(2H)-isoquinolone to a corresponding 4-alkoxycarbonyl-3,4-dihydro-1(2H)-isoquinolone;
  d) reacting said 4-alkoxycarbonyl-3,4-dihydro-1(2H)-isoquinolone with sodium hexamethyldisilazide and phenylselenyl chloride to give the corresponding selenide followed by oxidation of said selenide with hydrogen peroxide to give the corresponding alkyl 3-(2-(methoxycarbonylamino)phenyl)-1-oxo-1,2-dihydroisoquinoline-4-carboxylate;
  e) saponification of said alkyl 3-(2-(methoxycarbonylamino)phenyl)-1-oxo-1,2-dihydroisoquinoline-4-carboxylate with a base to give the corresponding dibenzo[c,h][1,6]naphthyridine-6,11(5H,12H)-dione; and
  f) when $R^6$ is chloro, chlorinating a dibenzo[c,h][1,6]naphthyridine-6,11(5H,12H)-dione of the preceding step with a chlorinating reagent comprising $POCl_3$ to give the corresponding 11-chlorodibenzo[c,h][1,6]-naphthyridin-6(5H)-one; or a combination of thereof.

* * * * *